(12) United States Patent  
Arzeno et al.

(10) Patent No.: US 8,642,601 B2  
(45) Date of Patent: Feb. 4, 2014

(54) INHIBITORS OF JNK

(75) Inventors: Humberto Bartolome Arzeno, Cupertino, CA (US); Lubov K. Filonova, Redwood City, CA (US); David Michael Goldstein, San Jose, CA (US); Leyi Gong, San Mateo, CA (US); Bradley E. Loe, Santa Cruz, CA (US); Erin M. O'Brien, Braintree, MA (US); Wylie Solang Palmer, Morristown, NJ (US); David Mark Rotstein, Sunnyvale, CA (US); Tania M. Silva, New York, NY (US); Yun-Chou Tan, Livingston, NJ (US)

(73) Assignee: Roche Palo Alto LLC, So. San Francisco, CA (US)

( * ) Notice: Subject to any disclaimer, the term of this patent is extended or adjusted under 35 U.S.C. 154(b) by 413 days.

(21) Appl. No.: 13/151,326

(22) Filed: Jun. 2, 2011

(65) Prior Publication Data  
US 2011/0301171 A1 Dec. 8, 2011

Related U.S. Application Data

(60) Provisional application No. 61/351,652, filed on Jun. 4, 2010.

(51) Int. Cl.  
A01N 43/54 (2006.01)  
C07D 239/12 (2006.01)  
C07D 401/04 (2006.01)  
C07D 471/04 (2006.01)  
C07D 471/22 (2006.01)  
C07D 487/04 (2006.01)  
A01N 43/56 (2006.01)  
A61K 31/415 (2006.01)

(52) U.S. Cl.  
USPC ............ 514/256; 514/257; 514/403; 514/406

(58) Field of Classification Search  
USPC .................. 514/256, 257, 403, 406  
See application file for complete search history.

(56) References Cited

FOREIGN PATENT DOCUMENTS

WO 2008/068171 6/2008  
WO 2009/138340 11/2009

OTHER PUBLICATIONS (International Search Report for PCT/EP2011/059005 Jul. 13, 2011).

Primary Examiner — Yong Chong

(57) ABSTRACT

Compounds of formula I

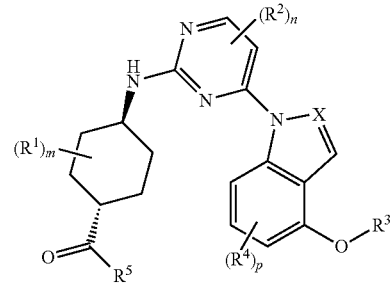

or pharmaceutically acceptable salts thereof, wherein $R^5$ is a group of formula (a) or (b):

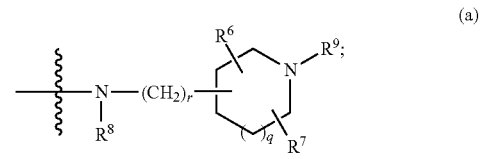

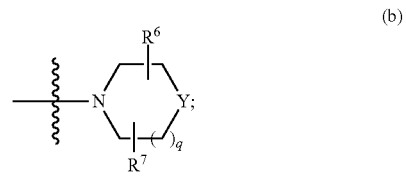

and wherein m, n, p, q, X, Y, $R^1$, $R^2$, $R^3$, $R^4$, $R^5$, $R^6$, $R^7$, $R^8$ and $R^9$ are as defined herein. The compounds and compositions disclosed herein are useful to modulate the activity of JNK and treat diseases associated with JNK activity.

16 Claims, No Drawings

INHIBITORS OF JNK

CROSS-REFERENCE TO RELATED APPLICATIONS

This application is entitled to the benefit of U.S. provisional patent application Ser. No. 61/351,652 filed on Jun. 4, 2010, the disclosure of which is incorporated herein by reference.

FIELD OF THE INVENTION

This invention relates generally to the fields of medicinal chemistry and treatment of inflammatory disorders. More particularly, the invention relates to prodrugs of JNK inhibitors, processes for making said inhibitors, and corresponding methods, formulations, and compositions for inhibiting JNK and treating JNK-mediated disorders, and the like.

BACKGROUND OF THE INVENTION

JNK The c-Jun N-terminal kinases (JNKs) are members of mitogen-activated protein kinase family along with p38 and extracellular signal-regulated kinases (ERKs). Three distinct genes (jnk1, jnk2 and jnk3) encoding 10 splice variants have been identified. JNK1 and JNK2 are expressed in a wide variety of tissues, whereas JNK3 is mainly expressed in neurons, and to a lesser extent in heart and testes. Members of JNK family are activated by pro-inflammatory cytokines such as tumor necrosis factor alpha (TNF-alpha) and interleukin-1beta (IL-1beta), as well as environmental stresses. The activation of JNKs is mediated by its upstream kinases, MKK4 and MKK7, via dual phosphorylation of Thr-183 and Tyr-185. It has been shown that MKK4 and MKK7 can be activated by the diverse upstream kinases, including MEKK1 and MEKK4, depending upon the external stimuli and cellular context. The specificity of JNK signaling is achieved by forming a JNK-specific signaling complex containing multiple components of the kinase cascade by use of scaffold proteins called JNK-interacting proteins. JNKs have been shown to play important roles in inflammation, T cell functions, apoptosis and cellular survival by phosphorylating specific substrates, including transcription factors such as c-Jun, the component of activator protein-1 (AP1) family, and ATF2, as well as non-transcription factors such as IRS-1 and Bcl-2. Over-activation of JNK is believed to be an important mechanism in autoimmune, inflammatory, metabolic, neurological diseases as well as cancer.

Rheumatoid arthritis (RA) is a systemic autoimmune disease characterized by chronic inflammation of the joints. In addition to the joint swelling and pain caused by the inflammatory process, most RA patients ultimately develop debilitating joint damage and deformation. Several lines of compelling pharmacological and genetic evidence in cellular and animal models strongly suggest the relevance and importance of the activated JNK in the pathogenesis of RA. First, abnormal activation of JNK was detected in both human arthritic joints from RA patients and rodent arthritic joints from animal models of arthritis. In addition, inhibition of JNK activation by selective JNK inhibitors blocked proinflammatory cytokines and MMP production in human synoviocytes, macrophages and lymphocytes. Importantly, administration of the selective JNK inhibitors in rats with adjuvant arthritis or in mice with collagen-induced arthritis effectively protected joints from destruction and significantly reduced paw swelling by inhibiting cytokine and collagenase expression.

Asthma is a chronic inflammatory disease of airways, characterized by the presence of a cellular inflammatory process and by bronchial hyper-responsiveness associated with structural changes of the airways. This disorder has been shown to be driven by many cell types in the airways, including T lymphocytes, eosinophils, mast cells, neutrophils and epithelial cells. JNKs have emerged as promising therapeutic targets for asthma based upon the recent proof-of-concept studies: it has been shown that JNK inhibitors significantly blocked RANTES production in activated human airway smooth cells. More importantly, the JNK inhibitors showed good efficacy in chronic rat and mouse models for their abilities to reduce cellular infiltration, inflammation, hyper-responsiveness, smooth muscle proliferation, and IgE production. These observations suggest important roles of JNKs in the allergic inflammation, airway remodeling process associated with hyper-responsiveness. Therefore, blockade of JNK activity is expected to be beneficial for the treatment of asthma.

Type 2 diabetes is the most serious and prevalent metabolic disease characterized by insulin resistance and insulin secretion impairment as a result of chronic low-level inflammation and abnormal lipid metabolism associated with oxidative stress. It has been reported that JNK activity is abnormally elevated in various diabetic target tissues under obese and diabetic conditions. Activation of the JNK pathway by pro-inflammatory cytokines and oxidative stresses negatively regulates insulin signaling via phosphorylation of insulin receptor substrate-1 (IRS-1) at $Ser^{307}$, therefore contributes to insulin resistance and glucose tolerance. Compelling genetic evidence came from elegant animal model studies using $jnk^{-/-}$ mice crossed with either genetic (ob/ob) obese mice or dietary obese mice. Loss of JNK1($JNK1^{-/-}$), but not JNK2 functions ($jnk2^{-/-}$), protected obese mice from body gains, increased steady-state levels of blood glucose, and decreased plasma insulin levels. These studies demonstrated the potential utility of JNK inhibitor in the treatment of obesity/type 2 diabetes.

Neurodegenerative diseases, such as Alzheimer's (AD), Parkinson's (PD) and Stroke are CNS diseases characterized by synaptic loss, neuronal atrophy and death. The JNK pathway leading to c-Jun activation has been shown to play a causal role in apoptosis of isolated primary embryonic neurons and multiple neuronal cell lines upon induction of a variety of stimuli. Over-activation of JNK was observed in human brains from AD patients or rodent brain sections derived from animal models of neurodegenerative diseases. For example, increased phospho-JNKs were detected in the post-mortem brains from the AD patients. Administration of JNK inhibitory peptide (JIP-1 peptide) in the rodent model of AD induced by β-amyloid peptide administration prevented the impairment of synaptic plasticity. In the animal models of PD (MPTP model), elevated phospho-MKK4 and phospho-JNKs were observed concomitantly with the neuronal cell death. Adenoviral gene transfer of JNK inhibitory peptide (JIP-1 peptide) into striatum of mice attenuated behavioral impairment by inhibiting MPTP-mediated JNK, c-Jun and caspase activation, therefore blocking neuronal cell death in the substantia nigra. In addition, in the animal model of ischemic stroke induced by glutamate excitotoxicity, mice deficient in JNK3, but not JNK1 or JNK2, were resistant to kainic acid (glutamate receptor agonist)-mediated seizure or neuronal death. These data suggest JNK3 was mainly responsible for glutamate excitotoxicity, an important component in ischemic conditions. Taken together, data has emerged suggesting JNKs as attractive target for multiple CNS diseases associated with neuronal cell death.

Uncontrolled cellular growth, proliferation and migration along with de-regulated angiogenesis lead to the formation of malignant tumors. The JNK signal transduction pathway may not act exclusively in apoptosis, sustained JNK activation leading to AP1 activation has recently been implicated to contribute to the cellular survival of specific cancer types such as glial tumors and BCL-ABL transformed B lymphoblasts. In the case of glial tumors, enhanced JNK/AP1 activity was seen in most of the primary brain tumor samples. For the transformed B lymphoblasts, BCL-ABL was shown to activate the JNK pathway which in turn up-regulated expression of anti-apoptotic bcl-2 gene. Interestingly, the multi-drug resistance and hyper-proliferation seen in treatment-refractory AML (acute myeloid leukemia) patients has been causally linked to the sustained JNK activity present in these AML samples. Activation of JNK in leukemic cells resulted in induced expression of efflux pumps such as mdr1 and MRP1 responsible for multidrug resistance. Also, genes with a survival benefit in response to oxidative stress including glutathione-S-transferase π and γ-glutamyl cysteine synthase were also upregulated by the activated JNK pathway.

Kidney diseases are characterized by loss of nephron function caused by progressive glomerulosclerosis and tubulointerstitial fibrosis. Renal disease may develop as a consequence of many conditions including inflammation, hypertension, diabetes, or acute tissue damage caused by antibiotics, contrast agents, or other nephrotoxic substances. JNK signaling has been shown to be upregulated in pathology specimens from many human renal diseases, including immune and non-immune mediated glomerulonephritis, diabetic nephropathy, hypertension, acute injury (1), and appears to play a signaling role in polycystic kidney disease (2). Compelling evidence for a central role of JNK and the therapeutic potential of JNK inhibitors is supported by studies in animal models of renal injury. JNK was increased in a rat anti-glomerular basement membrane induced glomerulonephritis model and renal function was improved by a specific inhibitor in both acute and chronic disease paradigms (3). JNK was also increased in the Dahl salt-sensitive hypertensive rat, a model of hypertensive renal disease (4), as well as in models of renal ischemia-reperfusion injury (5,6). The cellular mechanisms by which JNK may contribute to renal injury are, in part, by up-regulation of pro-inflammatory mediators in macrophages, as well as by activation of pro-fibrotic, and pro-apoptotic pathways directly in cells of the renal glomerulus and the tubular epithelium (7). The ability to improve renal function by inhibition of JNK in multiple disease models, suggests JNKs as attractive targets for therapy of renal diseases of various etiology.

SUMMARY OF THE INVENTION

The invention provides compounds of formula I

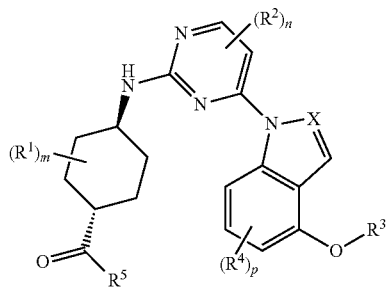

or pharmaceutically acceptable salts thereof, wherein:
m is from 0 to 2;
n is from 0 to 2;
p is from 0 to 3;
X is CH or N;
each $R^1$ is independently: hydrogen; or $C_{1-6}$alkyl;
each $R^2$ is independently: $C_{1-6}$alkyl; $C_{1-6}$alkoxy halo-$C_{1-6}$alkyl; or halo-$C_{1-6}$alkoxy;
$R^3$ is: $C_{1-6}$alkylsulfonyl-$C_{1-6}$alkyl; thiophenyl-1,1-oxide-$C_{1-6}$alkyl; or tetrahydrothiopyran-1,1-oxide-$C_{1-6}$alkyl;
each $R^4$ is independently: $C_{1-6}$alkyl; $C_{1-6}$alkoxy halo-$C_{1-6}$alkyl; or halo-$C_{1-6}$alkoxy;
$R^5$ is a group of formula (a) or (b):

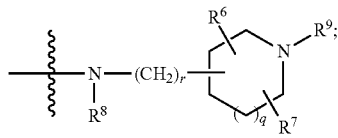

(a)

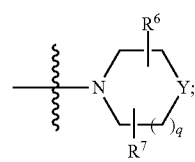

(b)

wherein:
q is 0 or 1;
r is 0 or 1;
Y is: $NR^9$; or $CR^{10}R^{11}$;
$R^6$ and $R^7$ each independently is: hydrogen; or $C_{1-6}$alkyl; or $R^6$ and $R^7$ together form a $C_{1-2}$alkylene;
$R^8$ is: hydrogen; or $C_{1-6}$alkyl;
$R^9$ is: hydrogen; or $C_{1-6}$alkyl;
$R^{10}$ is: hydrogen; or $C_{1-6}$alkyl; and
$R^{11}$ is: $C_{1-6}$alkyl; hydroxy-$C_{1-6}$alkyl; carboxy; carboxy-$C_{1-6}$alkyl; carboxy-$C_{1-6}$alkyl ester; or carboxy-$C_{1-6}$alkyl $C_{1-6}$alkyl ester.

The invention also provides methods of making the subject compounds, and methods of using the subject compounds for treatment of JNK-mediated diseases and conditions.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise. Thus, the phrase "'a" or "an" entity' as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., m, n, p, q, Q, r, $R^1$, $R^2$, $R^3$, $R^4$, X, $X^1$, $X^2$, $X^3$, $X^4$, $X^5$, $Y^1$, $Y^2$, $Z^1$, and $Z^2$) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "$\ldots$" drawn through a bond each refer to the point of attachment of a functional group or other chemical moiety to the rest of the molecule of which it is a part. Thus, for example:

MeC(=O)OR$^4$ wherein R$^4$=

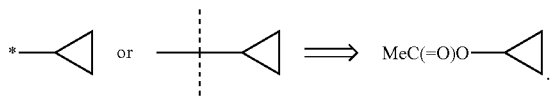

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of the invention may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —$CH_2CH$(i-Pr)$CH_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "alkylsulfonyl" as used herein means a group —$SO_2R$ wherein R is alkyl as defined herein.

The term "alkylsulfonylalkyl" as used herein means a group —R'$SO_2R$ wherein R is alkyl and R' is alkylene as defined herein. Exemplary alkylsulfonylalkyl include 3-methanesulfonyl-propoxy 2-methanesulfonyl-ethoxy and the like.

The term "tetrahydrothiophenyl-1,1-oxide-$C_{1-6}$alkyl" as used herein means a group —RR' wherein R is alkylene as defined herein and R' is tetrahydrothiophenyl-1,1-oxide. Exemplary tetrahydrothiophenyl-1,1-oxide-$C_{1-6}$alkyl include 1,1-dioxo-tetrahydro-1λ6-thiophen-3-ylmethyl and 2-(1,1-dioxo-tetrahydro-1λ6-thiophen-3-yl)-ethyl.

The term "tetrahydrothiopyran-1,1-oxide-$C_{1-6}$alkyl" as used herein means a group —RR' wherein R is alkylene as defined herein and R' is tetrahydrothiopyran-1,1-oxide. Exemplary tetrahydrothiopyran-1,1-oxide-$C_{1-6}$alkyl include 1,1-dioxo-hexahydro-1lambda*6*-thiopyran-3-ylmethyl and 2-(1,1-dioxo-hexahydro-1lambda*6*-thiopyran-3-yl)-ethyl.

The term "carboxy" as used herein means a group of formula —COOH.

The term "carboxy alkyl ester" as used herein means a group of formula —COOR wherein R is alkyl as defined herein.

The term "carboxy-alkyl" as used herein means a group of formula —R'—COOH wherein R' is alkylene as described herein.

The term "carboxy-alkyl alkyl ester" as used herein means a group of formula —R'—COOR wherein R is alkyl and R' is alkylene as described herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

The term "base" includes, but is not limited to, NaOH, KOH, LiOH and alkali metal carbonates such as potassium carbonate, sodium carbonate, lithium carbonate, sodium bicarbonate, cesium carbonate and the like.

"Cycloalkyl" or "carbocyclic ring" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Heterocycloalkyl lower alkyl" mean a moiety of the formula —$R^a$—$R^b$, where $R^a$ is lower alkylene and $R^b$ is heterocycloalkyl as defined herein.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocyclyl", "heterocycle", or "heterocycloalkyl" as used herein denotes a monovalent saturated cyclic radical, consisting of one or more rings, preferably one to two rings, of three to eight atoms per ring, incorporating one or more ring heteroatoms (chosen from N,O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The term "hydroxyalkyl" as used herein denotes an alkyl radical as herein defined wherein one to three hydrogen atoms on different carbon atoms is/are replaced by hydroxyl groups.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tent-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-$BuMe_2Si$ (TBDMS), triethylamine (TEA or $Et_3N$), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethyl-heptane-2,6-dione (TMHD), O-benzotriazol-1-yl-N,N,N', N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n), iso (i-), secondary (sec-), tertiary (tent-) and neo have their customary meaning when used with an alkyl moiety. (J. Rigaudy and D. P. Klesney, *Nomenclature in Organic Chemistry*, IUPAC 1979 Pergamon Press, Oxford.).

"Heteroaryl" means a monocyclic or bicyclic moiety of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, pyridazinyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof The terms "halo," "halogen," and "halide" are used interchangeably herein and refer to fluoro, chloro, bromo, and iodo.

"Haloalkyl" means alkyl as defined herein in which one or more hydrogen has been replaced with same or different halogen. The term "lower haloalkyl" denotes a straight or branched chain hydrocarbon residue containing 1 to 6 carbon atoms substituted with one or more halogen atom. Exemplary haloalkyls include —$CH_2Cl$, —$CH_2CF_3$, —$CH_2CCl_3$, —$CF_2CF_3$, —$CF_3$, and the like.

"Heterocyclyl" or "heterocycloalkyl" means a monovalent saturated moiety, consisting of one to two rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydroisoquinolinyl, tetrahydroquinolinyl, tetrahydrisoquinolinyl, and the like.

"Optionally substituted" means a substituent which is substituted independently with zero to three substituents selected from lower alkyl, halo, OH, cyano, amino, nitro, lower alkoxy, or halo-lower alkyl.

Preferred "oxidizing agents" include peracids like in-chloroperbenzoic acid (MCPBA) and peracetic acid, but other oxidizing agents like hydrogen peroxide, permanganate salts, or persulfate salts can be used to oxidize a thioether to a sulfone.

"Leaving group" means a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Optional" or "optionally" means that the subsequently described event or circumstance may but need not occur, and that the description includes instances where the event or circumstance occurs and instances in which it does not.

"Agonist" refers to a compound that enhances the activity of another compound or receptor site.

"Antagonist" refers to a compound that diminishes or prevents the action of another compound or receptor site.

The term "drug candidate" refers to a compound or preparation which is to be tested for possible effect in the treatment of a disease state in an animal, regardless of whether said drug candidate has any known biological activity.

The term "homologous" as used herein refers to a protein that performs substantially the same function in another subject species and shares substantial sequence identity, to the extent that they are recognized in the art as being different versions of the same protein, differing primarily in the species in which they are found. Thus, for example, human ERG, mouse ERG, and rat ERG are all considered homologous to each other.

"Modulator" means a molecule that interacts with a target. The interactions include, but are not limited to, agonist, antagonist, and the like, as defined herein.

"Disease" and "Disease state" means any disease, condition, symptom, disorder or indication.

The term "cell line" refers to a clone of immortalized mammalian cells. A "stable" cell line is a cell line that exhibits substantially consistent characteristics over time (e.g., with each doubling). A stable cell line within the scope of this invention provides a substantial proportion of cells that are capable of providing a seal resistance of greater than about 50 MOhm, a current amplitude of greater than about 200 pA, and provide a current amplitude that does not vary by more than approximately 20% over one hour under control conditions.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

It should be understood that all references to pharmaceutically acceptable salts include solvent addition forms (solvates) or crystal forms (polymorphs) as defined herein, of the same acid addition salt.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" includes mammals and birds. "Mammals" means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

"Pharmacological effect" as used herein encompasses effects produced in the subject that achieve the intended purpose of a therapy. For example, a pharmacological effect would be one that results in the prevention, alleviation or reduction of urinary incontinence in a treated subject.

"Disease state" means any disease, condition, symptom, or indication.

"Treating" or "treatment" of a disease state includes (i) preventing the disease state, i.e. causing the clinical symptoms of the disease state not to develop in a subject that may be exposed to or predisposed to the disease state, but does not yet experience or display symptoms of the disease state; (ii) inhibiting the disease state, i.e., arresting the development of the disease state or its clinical symptoms; or (iii) relieving the disease state, i.e., causing temporary or permanent regression of the disease state or its clinical symptoms.

All patents and publications identified herein are incorporated herein by reference in their entirety.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes.

Compounds of the Invention

The invention provides compounds of formula I:

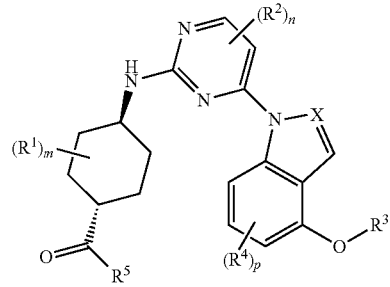

or pharmaceutically acceptable salts thereof,
wherein:
  m is from 0 to 2;
  n is from 0 to 2;
  p is from 0 to 3;
  X is CH or N;
  each $R^1$ is independently: hydrogen; or $C_{1-6}$alkyl;
  each $R^2$ is independently: $C_{1-6}$alkyl; $C_{1-6}$alkoxy halo-$C_{1-6}$alkyl; or halo-$C_{1-6}$alkoxy;
  $R^3$ is: $C_{1-6}$alkylsulfonyl-$C_{1-6}$alkyl; thiophenyl-1,1-oxide-$C_{1-6}$alkyl; or tetrahydrothiopyran-1,1-oxide-$C_{1-6}$alkyl;
  each $R^4$ is independently: $C_{1-6}$alkyl; $C_{1-6}$alkoxy halo-$C_{1-6}$alkyl; or halo-$C_{1-6}$alkoxy;

R⁵ is a group of formula (a) or (b):

(a)

$$\text{-N(R}^8\text{)-(CH}_2)_r\text{-[piperidine with R}^6, R^7, N\text{-R}^9\text{]}$$

(b)

$$\text{-N-[ring with R}^6, R^7, Y]_q$$

wherein:
q is 0 or 1;
r is 0 or 1;
Y is: NR⁹; or CR¹⁰R¹¹;
R⁶ and R⁷ each independently is: hydrogen; or $C_{1-6}$alkyl; or R⁶ and R⁷ together form a $C_{1-2}$alkylene;
R⁸ is: hydrogen; or $C_{1-6}$alkyl;
R⁹ is: hydrogen; or $C_{1-6}$alkyl;
R¹⁰ is: hydrogen; or $C_{1-6}$alkyl; and
R¹¹ is: $C_{1-6}$alkyl; hydroxy-$C_{1-6}$alkyl; carboxy; carboxy-$C_{1-6}$alkyl; carboxy-$C_{1-6}$alkyl ester; or carboxy-$C_{1-6}$alkyl $C_{1-6}$alkyl ester.

In certain embodiments of formula I, m is 0 or 1.
In certain embodiments of formula I, m is 0.
In certain embodiments of formula I, m is 1.
In certain embodiments of formula I, n is 0 or 1.
In certain embodiments of formula I, n is 0.
In certain embodiments of formula I, n is 1.
In certain embodiments of formula I, p is from 0 to 2.
In certain embodiments of formula I, p is 0 or 1.
In certain embodiments of formula I, p is 0.
In certain embodiments of formula I, p is 1.
In certain embodiments of formula I, q is 0.
In certain embodiments of formula I, q is 1.
In certain embodiments of formula I, r is 0.
In certain embodiments of formula I, r is 1.
In certain embodiments of formula I, X is CH.
In certain embodiments of formula I, X is N.
In certain embodiments of formula I, R¹ is hydrogen.
In certain embodiments of formula I, R¹ is $C_{1-6}$alkyl.
In certain embodiments of formula I, each R² is independently $C_{1-6}$alkyl, $C_{1-6}$alkoxy or halo.
In certain embodiments of formula I, each R² is independently $C_{1-6}$alkyl or halo.
In certain embodiments of formula I, R² is $C_{1-6}$alkyl.
In certain embodiments of formula I, R³ is $C_{1-6}$alkylsulfonyl-$C_{1-6}$alkyl.

In certain embodiments of formula I, R³ is tetrahydrothiophenyl-1,1-oxide-$C_{1-6}$alkyl.
In certain embodiments of formula I, R³ is tetrahydrothiopyran-1,1-oxide-$C_{1-6}$alkyl.
In certain embodiments of formula I, R³ is: 3-methanesulfonyl-propyl; or 1,1-dioxo-tetrahydro-1λ6-thiophen-3-ylmethyl.
In certain embodiments of formula I, R³ is 3-methanesulfonyl-propyl.
In certain embodiments of formula I, R³ is 1,1-dioxo-tetrahydro-1λ6-thiophen-3-ylmethyl.
In certain embodiments of formula I, each R⁴ is independently $C_{1-6}$alkyl or halo.
In certain embodiments of formula I, R⁴ is $C_{1-6}$alkyl.
In certain embodiments of formula I, R⁵ is a group of formula (a).
In certain embodiments of formula I, R⁵ is a group of formula (b).
In certain embodiments of formula I, R⁶ is hydrogen.
In certain embodiments of formula I, R⁶ is $C_{1-6}$alkyl.
In certain embodiments of formula I, R⁷ is hydrogen.
In certain embodiments of formula I, R⁷ is $C_{1-6}$alkyl.
In certain embodiments of formula I, R⁶ and R⁷ together form a $C_{1-2}$alkylene.
In certain embodiments of formula I, R⁶ and R⁷ together form methylene.
In certain embodiments of formula I, R⁶ and R⁷ together form ethylene.
In certain embodiments of formula I, R⁸ is hydrogen.
In certain embodiments of formula I, R⁸ is $C_{1-6}$alkyl.
In certain embodiments of formula I, Y is NR⁹.
In certain embodiments of formula I, Y is CR¹⁰R¹¹.
In certain embodiments of formula I, R⁹ is hydrogen.
In certain embodiments of formula I, R⁹ is $C_{1-6}$alkyl.
In certain embodiments of formula I, R¹⁰ is hydrogen.
In certain embodiments of formula I, R¹⁰ is $C_{1-6}$alkyl.
In certain embodiments of formula I, R¹¹ is: $C_{1-6}$alkyl; or hydroxy-$C_{1-6}$alkyl.
In certain embodiments of formula I, R¹¹ is $C_{1-6}$alkyl.
In certain embodiments of formula I, R¹¹ is hydroxy-$C_{1-6}$alkyl.
In certain embodiments of formula I, R¹¹ is carboxy.
In certain embodiments of formula I, R¹¹ is carboxy $C_{1-6}$alkyl ester.
In certain embodiments of formula I, R¹¹ is carboxy-$C_{1-6}$alkyl.
In certain embodiments of formula I, R¹¹ is carboxy-$C_{1-6}$alkyl-$C_{1-6}$alkyl ester.

Representative compounds encompassed by the present invention and within the scope of the invention are provided below in Table 1 together with melting point and IC50 affinity values for selected compounds.

TABLE 1

| # | Structure | Name (Autonom) | MP ° C. | IC50 |
|---|---|---|---|---|
| 1 | 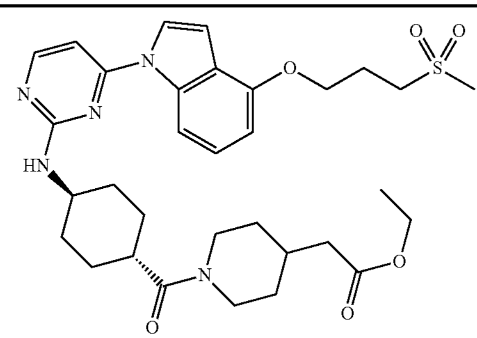 | [1-(4-{4-[4-(3-Methanesulfonyl-propoxy)-indol-1-yl]-pyrimidin-2-ylamino}-cyclohexanecarbonyl)-piperidin-4-yl]-acetic acid ethyl ester | 175.0-177.0 | 0.5496 |

TABLE 1-continued

| # | Structure | Name (Autonom) | MP ° C. | IC50 |
|---|---|---|---|---|
| 2 | 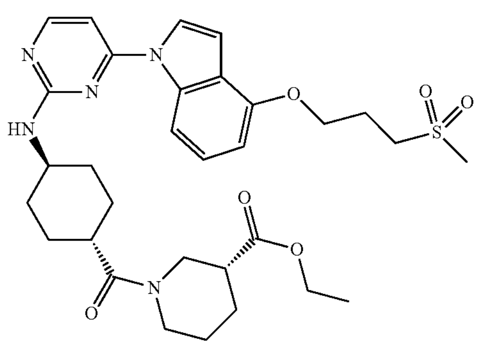 [SMILES: CCOC(=O)[C@@H]1CCCN(C(=O)[C@H]2CC[C@H](Nc3nccc(-n4ccc5c(OCCCS(C)(=O)=O)cccc54)n3)CC2)C1] | (R)-1-(4-{4-[4-(3-Methanesulfonyl-propoxy)-indol-1-yl]-pyrimidin-2-ylamino}-cyclohexanecarbonyl)-piperidine-3-carboxylic acid ethyl ester | 96.0-98.0 | 0.0734 |
| 3 | 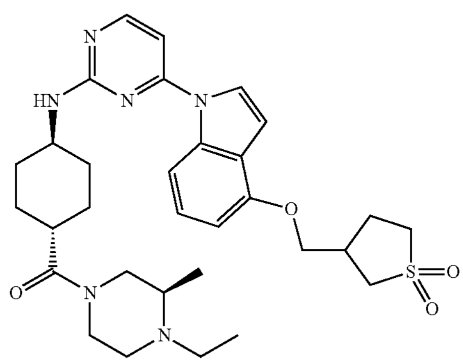 [SMILES: CCN1CCN(C(=O)[C@H]2CC[C@H](Nc3nccc(-n4ccc5c(OCC6CCS(=O)(=O)C6)cccc54)n3)CC2)C[C@H]1C] | (4-{4-[4-(1,1-Dioxo-tetrahydro-1$\lambda^6$-thiophen-3-ylmethoxy)-indol-1-yl]-pyrimidin-2-ylamino}-cyclohexyl)-((R)-4-ethyl-3-methyl-piperazin-1-yl)-methanone | 225.0 (HCl salt) | 0.0459 |
| 4 | 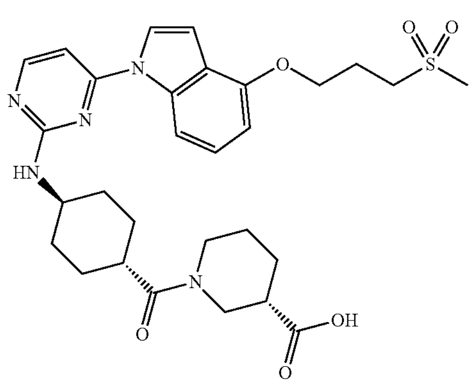 [SMILES: CS(=O)(=O)CCCOc1cccc2c1ccn2-c1ccnc(N[C@H]2CC[C@H](C(=O)N3CCC[C@H](C(=O)O)C3)CC2)n1] | (S)-1-(4-{4-[4-(3-Methanesulfonyl-propoxy)-indol-1-yl]-pyrimidin-2-ylamino}-cyclohexanecarbonyl)-piperidine-3-carboxylic acid | 270.0-276.0 | 0.1074 |
| 5 | 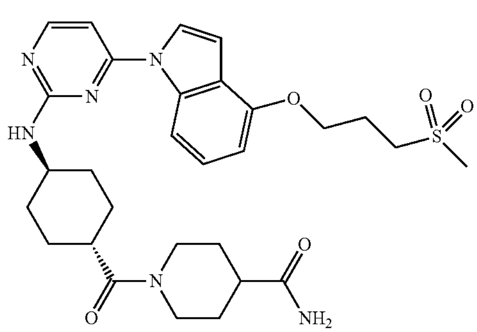 [SMILES: CS(=O)(=O)CCCOc1cccc2c1ccn2-c1ccnc(N[C@H]2CC[C@H](C(=O)N3CCC(C(N)=O)CC3)CC2)n1] | 1-(4-{4-[4-(3-Methanesulfonyl-propoxy)-indol-1-yl]-pyrimidin-2-ylamino}-cyclohexanecarbonyl)-piperidine-4-carboxylic acid amide | 219.0-221.0 | 0.0917 |

TABLE 1-continued

| # | Structure | Name (Autonom) | MP ° C. | IC50 |
|---|---|---|---|---|
| 6 | 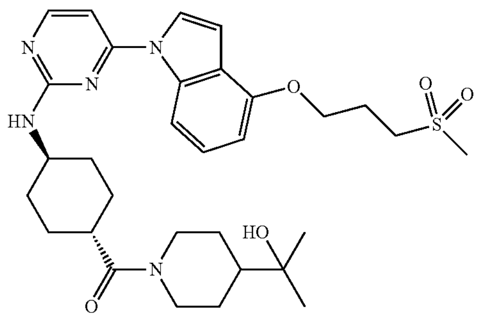 [SMILES: CC(C)(O)C1CCN(C(=O)[C@H]2CC[C@H](Nc3nccc(-n4ccc5c(OCCCS(C)(=O)=O)cccc54)n3)CC2)CC1] | [4-(1-Hydroxy-1-methyl-ethyl)-piperidin-1-yl]-(4-{4-[4-(3-methanesulfonyl-propoxy)-indol-1-yl]-pyrimidin-2-ylamino}-cyclohexyl)-methanone | 196.0-198.0 | 0.086 |
| 7 | 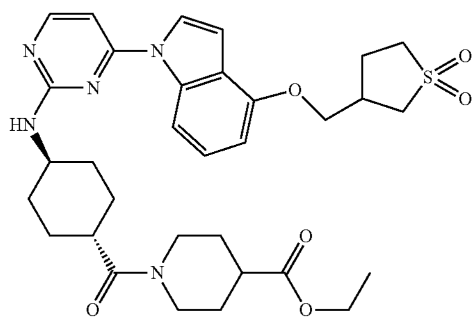 [SMILES: CCOC(=O)C1CCN(C(=O)[C@H]2CC[C@H](Nc3nccc(-n4ccc5c(OCC6CCS(=O)(=O)C6)cccc54)n3)CC2)CC1] | 1-(4-{4-[4-(1,1-Dioxo-tetrahydro-1λ⁶-thiophen-3-ylmethoxy)-indol-1-yl]-pyrimidin-2-ylamino}-cyclohexanecarbonyl)-piperidine-4-carboxylic acid ethyl ester | 209.0-211.0 | 0.0514 |
| 8 | 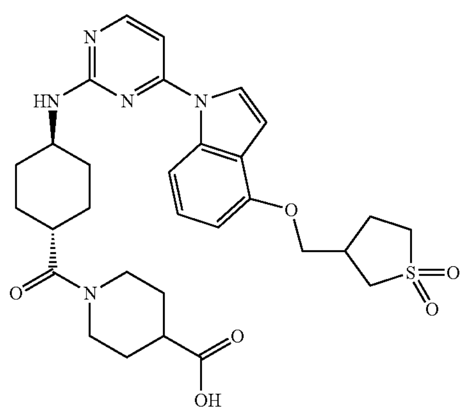 [SMILES: O=C(O)C1CCN(C(=O)[C@H]2CC[C@H](Nc3nccc(-n4ccc5c(OCC6CCS(=O)(=O)C6)cccc54)n3)CC2)CC1] | 1-(4-{4-[4-(1,1-Dioxo-tetrahydro-1λ⁶-thiophen-3-ylmethoxy)-indol-1-yl]-pyrimidin-2-ylamino}-cyclohexanecarbonyl)-piperidine-4-carboxylic acid | 172.0-174.0 | 0.0708 |
| 9 | 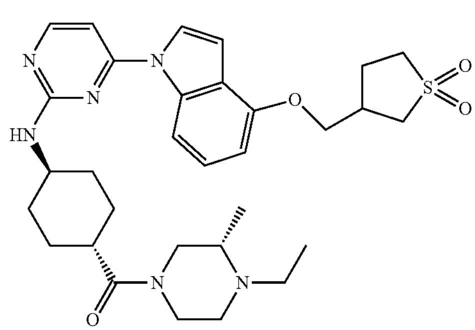 [SMILES: CCN1CCN(C(=O)[C@H]2CC[C@H](Nc3nccc(-n4ccc5c(OCC6CCS(=O)(=O)C6)cccc54)n3)CC2)C[C@@H]1C] | (4-{4-[4-(1,1-Dioxo-tetrahydro-1λ⁶-thiophen-3-ylmethoxy)-indol-1-yl]-pyrimidin-2-ylamino}-cyclohexyl)-((S)-4-ethyl-3-methyl-piperazin-1-yl)-methanone | 198.0-204.0 (HCl salt) | 0.0194 |

TABLE 1-continued

| # | Structure | Name (Autonom) | MP ° C. | IC50 |
|---|---|---|---|---|
| 10 | 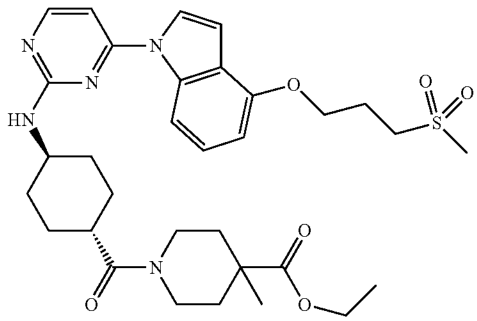 [SMILES: CCOC(=O)C1(C)CCN(C(=O)[C@H]2CC[C@H](Nc3nccc(-n4ccc5c(OCCCS(C)(=O)=O)cccc54)n3)CC2)CC1] | 1-(4-{4-[4-(3-Methanesulfonyl-propoxy)-indol-1-yl]-pyrimidin-2-ylamino}-cyclohexanecarbonyl)-4-methyl-piperidine-4-carboxylic acid ethyl ester | 171.0-173.0 | 0.0584 |
| 11 | 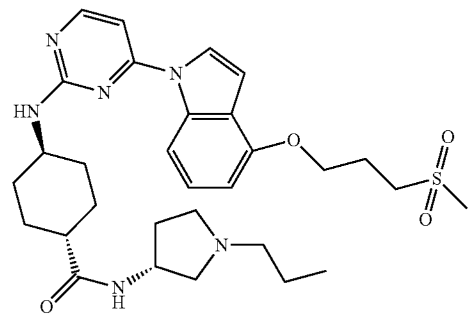 [SMILES: CCCN1CC[C@@H](NC(=O)[C@H]2CC[C@H](Nc3nccc(-n4ccc5c(OCCCS(C)(=O)=O)cccc54)n3)CC2)C1] | 4{4-[4-(3-Methanesulfonyl-propoxy)-indol-1-yl]-pyrimidin-2-ylamino}-cyclohexanecarboxylic acid ((R)-1-propyl-pyrrolidin-3-yl)-amide | 140.0-142.0 (HCl salt) | 0.1642 |
| 12 | 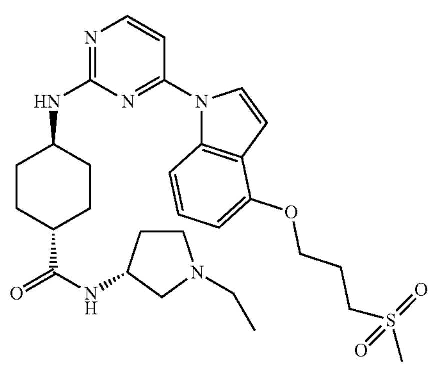 [SMILES: CCN1CC[C@@H](NC(=O)[C@H]2CC[C@H](Nc3nccc(-n4ccc5c(OCCCS(C)(=O)=O)cccc54)n3)CC2)C1] | 4-{4-[4-(3-Methanesulfonyl-propoxy)-indol-1-yl]-pyrimidin-2-ylamino}-cyclohexanecarboxylic acid ((R)-1-ethyl-pyrrolidin-3-yl)-amide | 229.0-231.0 | 0.0938 |
| 13 | 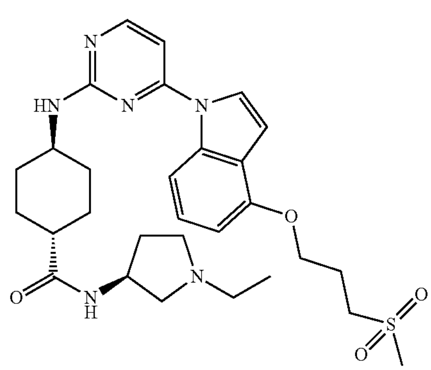 [SMILES: CCN1CC[C@H](NC(=O)[C@H]2CC[C@H](Nc3nccc(-n4ccc5c(OCCCS(C)(=O)=O)cccc54)n3)CC2)C1] | 4-{4-[4-(3-Methanesulfonyl-propoxy)-indol-1-yl]-pyrimidin-2-ylamino}-cyclohexanecarboxylic acid ((S)-1-ethyl-pyrrolidin-3-yl)-amide | 160.0-162.0 (HCl salt) | 0.3356 |

TABLE 1-continued

| # | Structure | Name (Autonom) | MP ° C. | IC50 |
|---|---|---|---|---|
| 14 | 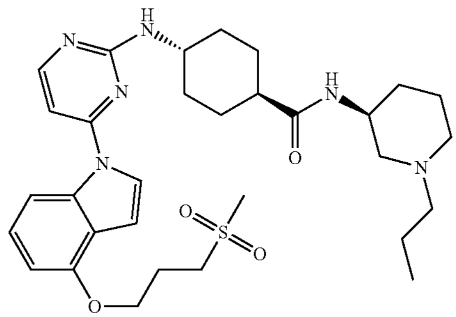 [SMILES: CCCN1CCC[C@H](NC(=O)[C@H]2CC[C@H](Nc3nccc(-n4ccc5c(OCCCS(C)(=O)=O)cccc54)n3)CC2)C1] | 4-{4-[4-(3-Methanesulfonyl-propoxy)-indol-1-yl]-pyrimidin-2-ylamino}-cyclohexanecarboxylic acid ((R)-1-propyl-piperidin-3-yl)-amide | 185.0-190.0 (HCl salt) | 0.0898 |
| 15 | 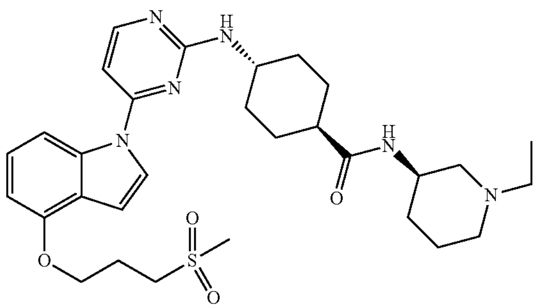 [SMILES: CCN1CCC[C@@H](NC(=O)[C@H]2CC[C@H](Nc3nccc(-n4ccc5c(OCCCS(C)(=O)=O)cccc54)n3)CC2)C1] | 4-{4-[4-(3-Methanesulfonyl-propoxy)-indol-1-yl]-pyrimidin-2-ylamino}-cyclohexanecarboxylic acid ((R)-1-ethyl-piperidin-3-yl)-amide | 180.0-185.0 (HCl salt) | |
| 16 | 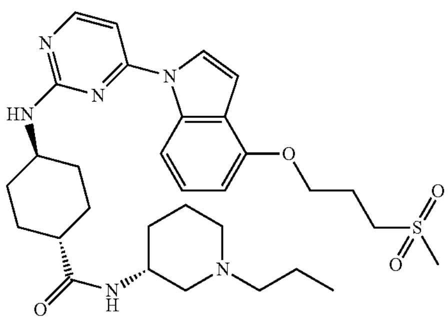 [SMILES: CCCN1CCC[C@@H](NC(=O)[C@H]2CC[C@H](Nc3nccc(-n4ccc5c(OCCCS(C)(=O)=O)cccc54)n3)CC2)C1] | 4-{4-[4-(3-Methanesuflonyl-propoxy)-indol-1-yl]-pyrimidin-2-ylamino}-cyclohexanecarboxylic acid ((S)-1-propyl-piperidin-3-yl)-amide | 185.0-190.0 | 0.163 |
| 17 | 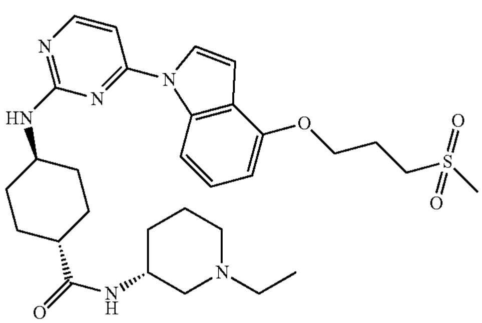 [SMILES: CCN1CCC[C@@H](NC(=O)[C@H]2CC[C@H](Nc3nccc(-n4ccc5c(OCCCS(C)(=O)=O)cccc54)n3)CC2)C1] | 4-{4-[4-(3-Methanesulfonyl-propoxy)-indol-1-yl]-pyrimidin-2-ylamino}-cyclohexanecarboxylic acid ((S)-1-ethyl-piperidin-3-yl)-amide | 180.0-185.0 | 0.1158 |
| 18 | 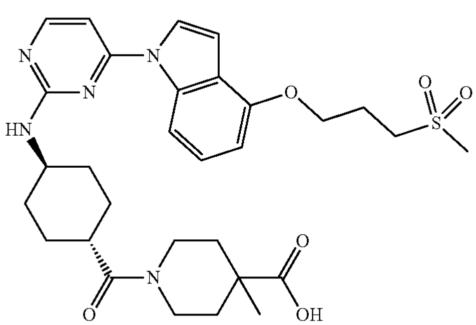 [SMILES: CC1(C(=O)O)CCN(C(=O)[C@H]2CC[C@H](Nc3nccc(-n4ccc5c(OCCCS(C)(=O)=O)cccc54)n3)CC2)CC1] | 1-(4-{4-[4-(3-Methanesulfonyl-propoxy)-indol-1-yl]-pyrimidin-2-ylamino}-cyclohexanecarbonyl)-4-methyl-piperidine-4-carboxylic acid | 174.0-174.0 | 0.1529 |

TABLE 1-continued

| # | Structure | Name (Autonom) | MP °C. | IC50 |
|---|---|---|---|---|
| 19 | 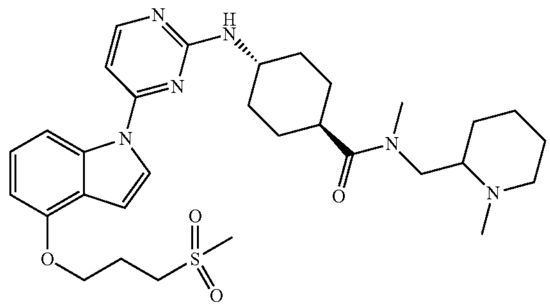 [SMILES: CN(CC1CCCCN1C)C(=O)[C@H]1CC[C@H](Nc2nccc(-n3ccc4c(OCCCS(C)(=O)=O)cccc43)n2)CC1] | 4-{4-[4-(3-Methanesulfonyl-propoxy)-indol-1-yl]-pyrimidin-2-ylamino}-cyclohexanecarboxylic acid methyl-(1-methyl-piperidin-2-ylmethyl)-amide | | 0.0796 |
| 20 | 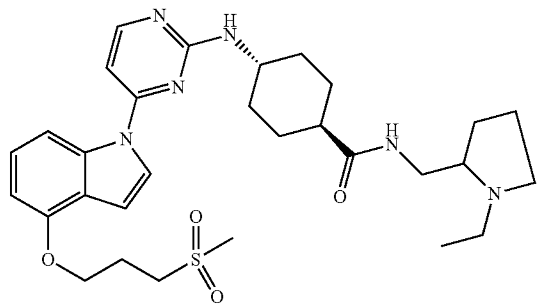 [SMILES: CCN1CCCC1CNC(=O)[C@H]1CC[C@H](Nc2nccc(-n3ccc4c(OCCCS(C)(=O)=O)cccc43)n2)CC1] | 4-{4-[4-(3-Methanesulfonyl-propoxy)-indol-1-yl]-pyrimidin-2-ylamino}-cyclohexanecarboxylic acid (1-ethyl-pyrrolidin-2-ylmethyl)-amide | | 0.081 |
| 21 | 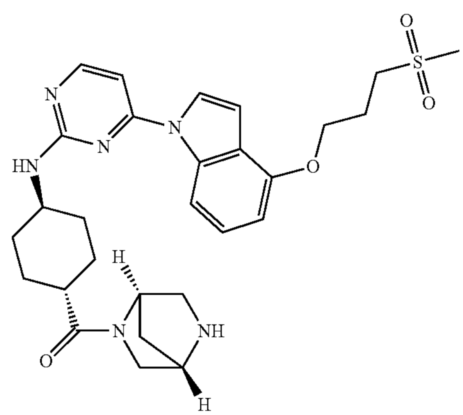 [SMILES: CS(=O)(=O)CCCOc1cccc2c1ccn2-c1ccnc(N[C@H]2CC[C@H](C(=O)N3C[C@@H]4C[C@@H]3CN4)CC2)n1] | (1R,4S)-2,5-Diaza-bicyclo[2.2.1]hept-2-yl-(4-{4-[4-(3-methanesulfonyl-propoxy)-indol-1-yl]-pyrimidin-2-ylamino}-cyclohexyl)-methanone | | 0.1447 |
| 22 | 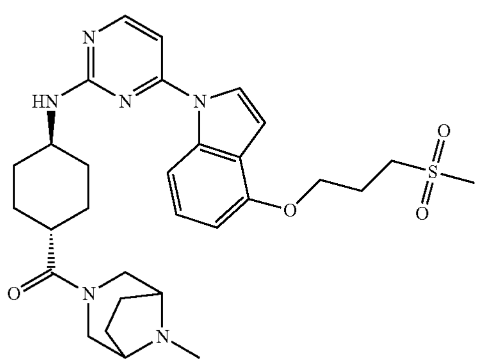 [SMILES: CN1C2CCC1CN(C(=O)[C@H]1CC[C@H](Nc3nccc(-n4ccc5c(OCCCS(C)(=O)=O)cccc54)n3)CC1)C2] | 4-{4-[4-(3-Methanesulfonyl-propoxy)-indol-1-yl]-pyrimidin-2-ylamino}-cyclohexyl)-(8-methyl-3,8-diaza-bicyclo[3.2.1]oct-3-yl)-methanone | | 0.0998 |

TABLE 1-continued

| # | Structure | Name (Autonom) | MP °C. | IC50 |
|---|---|---|---|---|
| 23 | 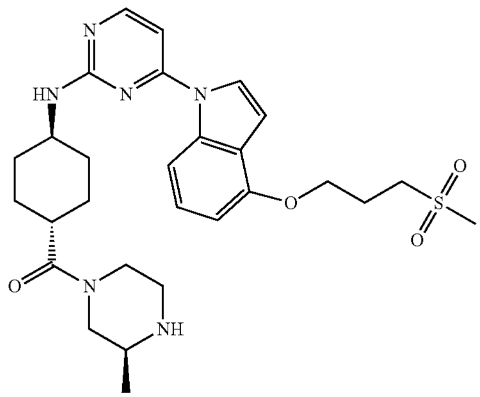 [SMILES: C[C@H]1CN(C(=O)[C@H]2CC[C@H](Nc3nccc(-n4ccc5c(OCCCS(C)(=O)=O)cccc54)n3)CC2)CCN1] | (4-{4-[4-(3-Methanesulfonyl-propoxy)-indazol-1-yl]-pyrimidin-2-ylamino}-cyclohexyl)-((S)-3-methyl-piperazin-1-yl)-methanone | | 0.073 |
| 24 | 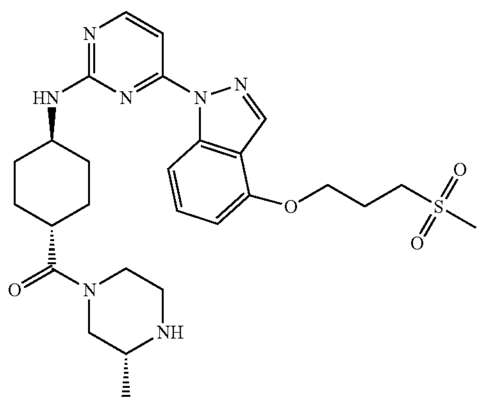 [SMILES: C[C@@H]1CN(C(=O)[C@H]2CC[C@H](Nc3nccc(-n4ncc5c(OCCCS(C)(=O)=O)cccc54)n3)CC2)CCN1] | (4-{4-[4-(3-Methanesulfonyl-propoxy)-indazol-1-yl]-pyrimidin-2-ylamino}-cyclohexyl)-((R)-3-methyl-piperazin-1-yl)-methanone | 245.0-250.0 (HCl salt) | 0.0597 |
| 25 | 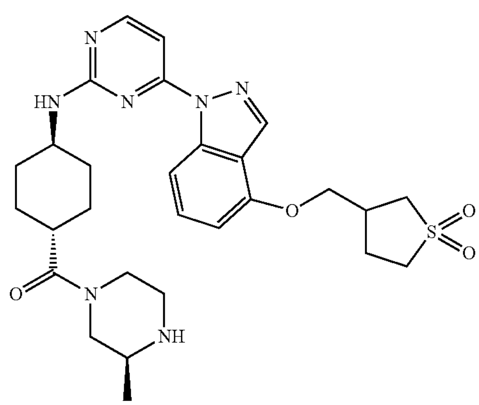 [SMILES: C[C@H]1CN(C(=O)[C@H]2CC[C@H](Nc3nccc(-n4ncc5c(OCC6CCS(=O)(=O)C6)cccc54)n3)CC2)CCN1] | (4-{4-[4-(1,1-Dioxo-tetrahydro-1$\lambda^6$-thiophen-3-ylmethoxy)-indazol-1-yl]-pyrimidin-2-ylamino}-cyclohexyl)-((S)-3-methyl-piperazin-1-yl)-methanone | 245.0-250.0 (HCl salt) | 0.0458 |
| 26 | 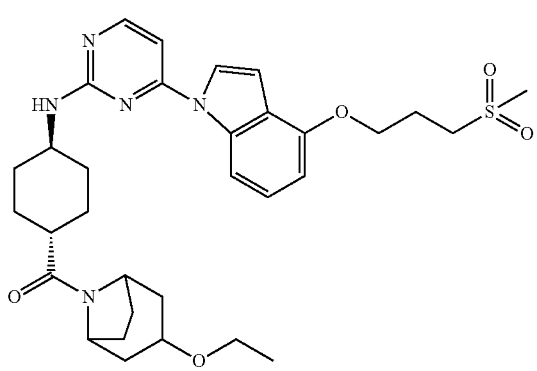 [SMILES: CCOC1CC2CCC(C1)N2C(=O)[C@H]1CC[C@H](Nc2nccc(-n3ccc4c(OCCCS(C)(=O)=O)cccc43)n2)CC1] | (3-Ethoxy-8-aza-bicyclo[3.2.1]oct-8-yl)-(4-{4-[4-(3-methanesulfonyl-propoxy)-indol-1-yl]-pyrimidin-2-ylamino}-cyclohexyl)-methanone; compound with formic acid | 125.0-130.0 (formate salt) | 0.0894 |

TABLE 1-continued

| # | Structure | Name (Autonom) | MP ° C. | IC50 |
|---|---|---|---|---|
| 27 | 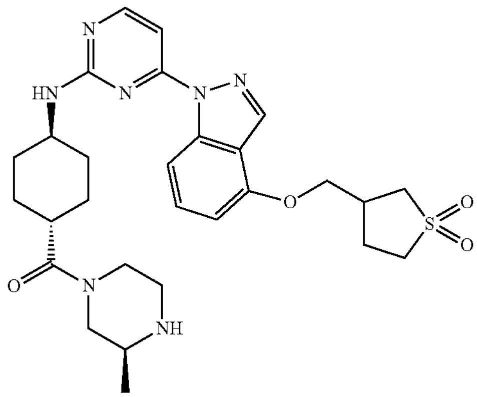 [SMILES: C[C@H]1CN(C(=O)[C@H]2CC[C@H](Nc3nccc(-n4ncc5c(OCC6CCS(=O)(=O)C6)cccc54)n3)CC2)CCN1] | (4-{4-[4-(1,1-Dioxo-tetrahydro-1λ⁶-thiophen-3-ylmethoxy)-indazol-1-yl]-pyrimidin-2-ylamino}-cyclohexyl)-((S)-3-methyl-piperazin-1-yl)-methanone | 245.0-250.0 (HCl salt) | 0.0606 |
| 28 | 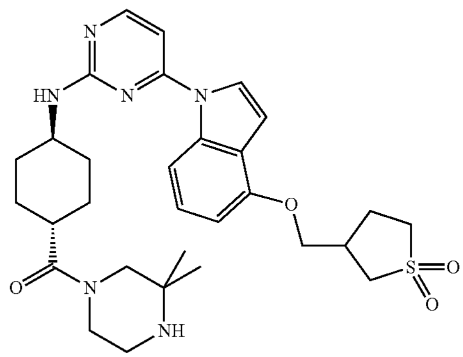 [SMILES: CC1(C)CN(C(=O)[C@H]2CC[C@H](Nc3nccc(-n4ccc5c(OCC6CCS(=O)(=O)C6)cccc54)n3)CC2)CCN1] | (3,3-Dimethyl-piperazin-1-yl)-(4-{4-[4-(1,1-dioxo-tetrahydro-1λ⁶-thiophen-3-ylmethoxy)-indol-1-yl]-pyrimidin-2-ylamino}-cyclohexyl)-methanone | >300 (HCl salt) | 0.0978 |
| 29 | 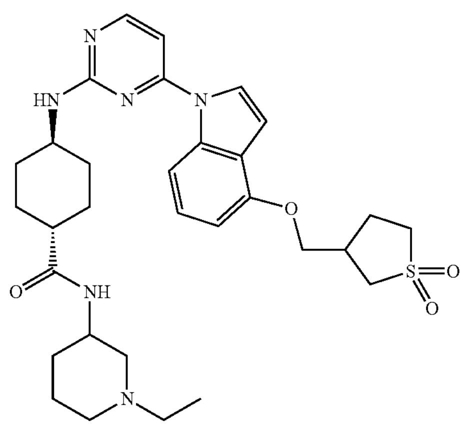 [SMILES: CCN1CCCC(NC(=O)[C@H]2CC[C@H](Nc3nccc(-n4ccc5c(OCC6CCS(=O)(=O)C6)cccc54)n3)CC2)C1] | 4-{4-[4-(1,1-Dioxo-tetrahydro-1λ⁶-thiophen-3-ylmethoxy)-indol-1-yl]-pyrimidin-2-ylamino}-cyclohexanecarboxylic acid (1-ethyl-piperidin-3-yl)-amide | 205.0-210.0 (HCl salt) | 0.0928 |
| 30 | 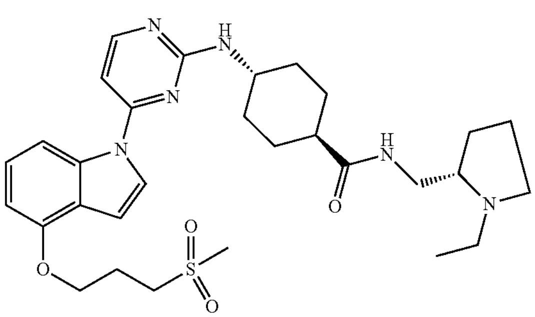 | 4-{4-[4-(3-Methanesulfonyl-propoxy)-indol-1-yl]-pyrimidin-2-ylamino}-cyclohexanecarboxylic acid ((S)-1-ethyl-pyrrolidin-2-ylmethyl)-amide | | 0.0854 |

TABLE 1-continued

| # | Structure | Name (Autonom) | MP ° C. | IC50 |
|---|---|---|---|---|
| 31 | 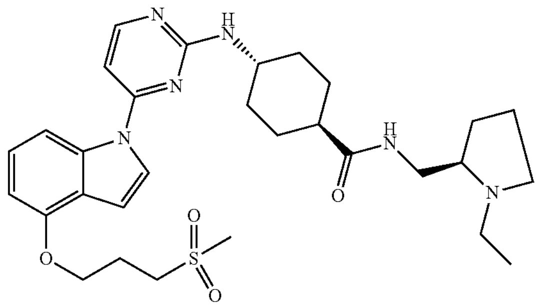 [SMILES: CCN1CCC[C@@H]1CNC(=O)[C@H]1CC[C@H](Nc2nccc(-n3ccc4c(OCCCS(C)(=O)=O)cccc43)n2)CC1] | 4-{4-[4-(3-Methanesulfonyl-propoxy)-indol-1-yl]-pyrimidin-2-ylamino}-cyclohexanecarboxylic acid ((R)-1-ethyl-pyrrolidin-2-ylmethyl)-amide | | 0.0977 |

Methods

In one aspect, the application provides a method of treating a JNK-mediated disorder in a subject having a JNK-mediated disorder, said method comprising administering to a subject in need thereof a therapeutically effective amount of any of the above compounds.

In certain embodiments of the method of treating a JNK-mediated disorder, the JNK-mediated disorder is characterized by cellular proliferation.

In certain embodiments of the method of treating a JNK-mediated disorder, the JNK-mediated disorder is arthritis.

In certain embodiments of the method of treating a JNK-mediated disorder, the arthritis is rheumatoid arthritis.

In certain embodiments of the method of treating a JNK-mediated disorder, the JNK-mediated disorder is asthma.

In certain embodiments of the method of treating a JNK-mediated disorder, the JNK-mediated disorder is diabetes.

In certain embodiments of the method of treating a JNK-mediated disorder, the JNK-mediated disorder is Alzheimer's disease.

In certain embodiments of the method of treating a JNK-mediated disorder, the JNK-mediated disorder is Parkinson's disease.

In certain embodiments of the method of treating a JNK-mediated disorder, the JNK-mediated disorder is ischemic stroke.

In certain embodiments of the method of treating a JNK-mediated disorder, the JNK-mediated disorder is cancer.

In certain embodiments of the method for treating a JNK-mediated disorder, wherein the JNK-mediated disorder is cancer, the cancer is brain cancer.

In certain embodiments of the method for treating a JNK-mediated disorder, wherein the JNK-mediated disorder is cancer, the cancer is leukemia.

In one aspect, the application provides a pharmaceutical composition comprising the compound of any one of the above embodiments, admixed with at least one pharmaceutically acceptable carrier, excipient or diluent.

Utility

The compounds of this invention are JNK modulators and as such are expected to be effective in the treatment of a wide range of JNK mediated disorders. Exemplary JNK mediated disorders include, but are not limited to, autoimmune disorders, inflammatory disorders, metabolic disorders, neurological disease, and cancer. Accordingly, compounds of the invention can be used to treat one or more of such disorders. In some embodiments, compounds of the invention can be used to treat a JNK mediated disorder such as rheumatoid arthritis, asthma, type II diabetes, Alzheimer's disease, Parkinson's disease or stroke.

Administration and Pharmaceutical Compositions

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, sub-cutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use.

Formulations containing about one (1) mg of active ingredient or, more broadly, about 0.01 to about one hundred (100) mg, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may also be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacyclo-heptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Additional objects, advantages, and novel features of this invention will become apparent to those skilled in the art upon examination of the following examples thereof, which are not intended to be limiting.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1-15; *Rodd's Chemistry of Carbon Compounds,* Elsevier Science Publishers, 1989, Volumes 1-5 and Supplementals; and *Organic Reactions,* Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula I, wherein R is lower alkyl and may be the same or different upon each occurrence, and m, n, p, q, r, X, $R^1$, $R^2$, $R^3$, $R^4$, $R^5$, $R^6$, $R^7$, $R^8$ and $R^9$ are as defined herein.

SCHEME A

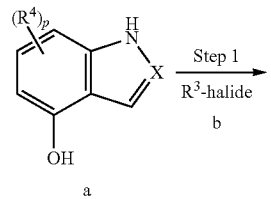

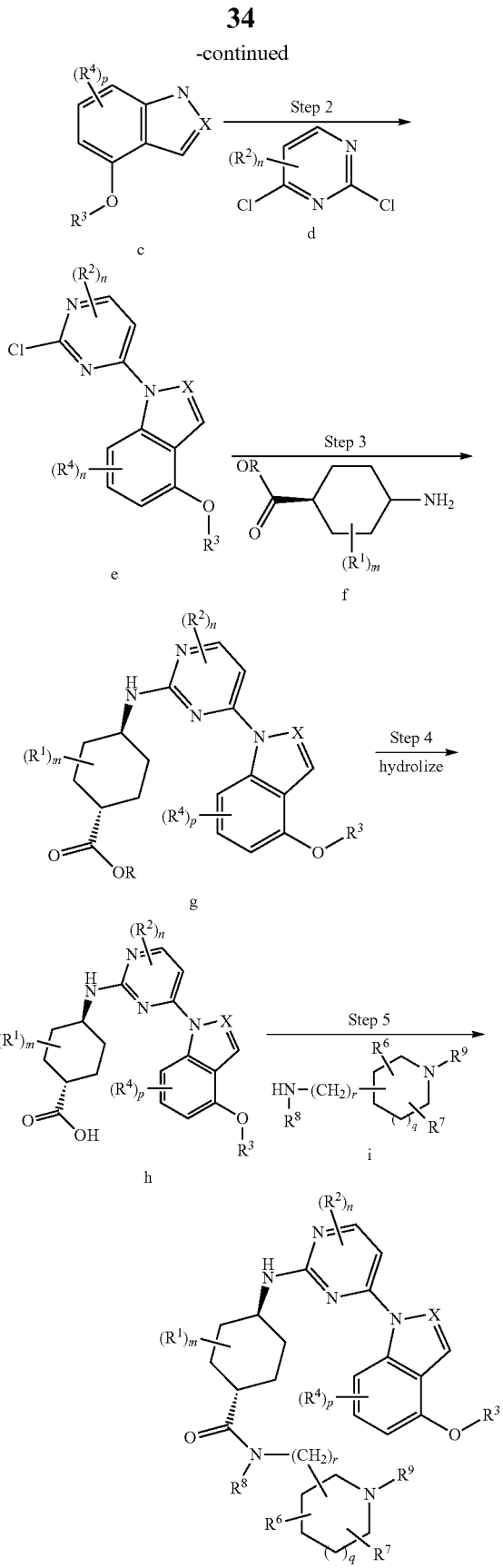

In step 1 of Scheme A, an O-alkylation reaction occurs wherein hydroxyindole compound a is reacted with halide compound b to afford indole compound c. The reaction may be carried out, for example, in the presence of potassium carbonate and potassium iodide in a polar aprotic solvent such as acetonitrile.

In step 2, indole c is reacted with dichloropyrimidine d to yield indole pyrimidine compound e. The reaction of step 2 may be effected in the presence of HOBt and potassium carbonate under polar solvent conditions.

In step 3, compound e is reacted with cyclohexylamine f to afford indole pyrimidine amine compound g. The reaction of step 3 may be carried out with potassium carbonate present under polar solvent conditions.

The carboxylate group of compound g undergoes hydrolysis in step 4 to provide the corresponding carboxylic acid compound h. Hydrolysis in the step may be achieved, for example, in the presence of base such as sodium hydroxide and under polar protic solvent conditions.

An amide formation occurs in step 5 wherein compound h is reacted with amine i to give amide compound j, which is a compound of formula I in accordance with the invention. Amide formation may be carried out via an acid chloride intermediate (not shown), or by using various amide coupling reagents such as ECDI or other carbodiimide.

Many variations on the procedure of Scheme A are possible and will suggest themselves to those skilled in the art. Specific details for producing compounds of the invention are described in the following Examples.

The following abbreviations may be used in the Preparations and Examples below.

List of Abbreviations
Ac$_2$O Acetic anhydride
AcOH Acetic acid
BOP Benzotriazole-1-yl-oxy-tris-(dimethylamino)-phosphonium hexafluorophosphate
DBU 1,8-Diazabicyclo[5.4.0]undec-7-ene
DCE 1,2-Dichloroethane
DCM Dichloromethane/Methylene chloride
DIPEA Diisopropylethylamine
DMA Dimethyl Acetamide
DMF N,N-dimethylformamide
DMSO Dimethyl sulfoxide
EDCI 1-(3-Dimethylaminopropyl)-3-ethylcarbodiimide hydrochloride
Et$_2$O Diethyl ether
EtOH Ethanol/Ethyl alcohol
EtOAc Ethyl acetate
HOBt 1-Hydroxybenzotriazole
LDA Lithium diisopropylamide
LiHMDS Lithium bis(trimethylsilyl)amide
m-CPBA 3-Chloroperoxybenzoic acid
MeOH Methanol/Methyl alcohol
MW Microwaves
NMP 1-Methyl-2-pyrrolidinone
PMB 4-Methoxy benzyl
PyBOP benzotriazol-1-yl-oxytripyrrolidinophosphonium hexafluorophosphate
RT Room temperature
TBME tert-Butyl methyl ether
TFA Trifluoroacetic acid
Tf$_2$O Trifluoromethanesulfonic anhydride
THF Tetrahydrofuran
TLC Thin layer chromatography

EXAMPLES

The following preparations and examples are given to enable those skilled in the art to more clearly understand and to practice the present invention. They should not be considered as limiting the scope of the invention, but merely as being illustrative and representative thereof.

Example 1

(1,1-Dioxo-tetrahydro-1lambda*6*-thiophen-3-yl)-methanol

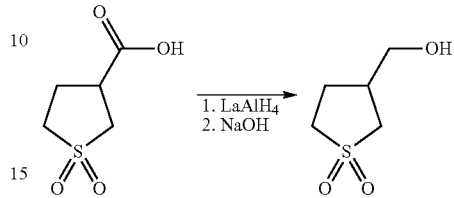

To a solution of 1,1-dioxo-tetrahydro-1lambda*6*-thiophene-3-carboxylic acid (5.0 g) in THF (100 mL) was added LAH (35 mL of 1M THF solution) drop-wise. The mixture was stirred at room temperature for five hours and then cooled in an ice bath. Water (3 mL) and NaOH (6 mL of 15% aqueous solution) were added, and the mixture was stirred a room temperature for 60 hours. The mixture was filtered and the filtrated was concentrated under reduced pressure to give 3.59 g of (1,1-dioxo-tetrahydro-1lambda*6*-thiophen-3-yl)-methanol.

Example 2

Toluene-4-sulfonic acid 1,1-dioxo-tetrahydro-1lambda*6*-thiophen-3-ylmethyl ester

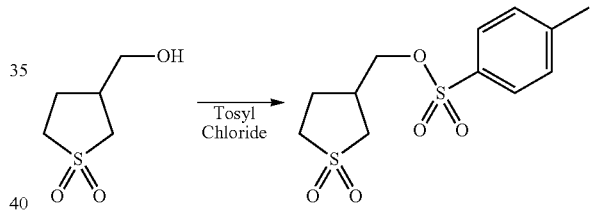

A mixture of (1,1-dioxo-tetrahydro-1lambda*6*-thiophen-3-yl)-methanol (3.59 g), 4-toluenesulfonyl chloride (9.11 g) and pyridine 5.8 mL) in chloroform (50 mL) was heated to 60° C. and stirred overnight. The reaction mixture was cooled and diluted with 100 mL 1N HCl and extracted with methylene chloride. The combined organic extracts were washed with brine, dried (MgSO$_4$), filtered and concentrated under reduced pressure. The residue was purified by flash chromatography (60% EtOAc in hexanes) to give 4.012 g of toluene-4-sulfonic acid 1,1-dioxo-tetrahydro-1lambda*6*-thiophen-3-ylmethyl ester.

Example 3

4-(3-Methylsulfanyl-propoxy)-1-(2-methylsulfanyl-pyrimidin-4-yl)-1H-indole

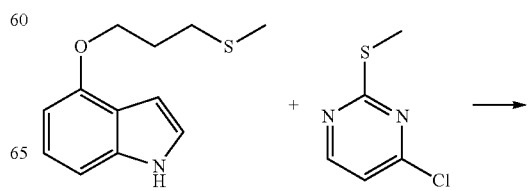

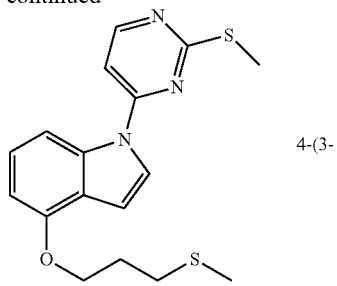

Methylsulfanyl-propoxy)-1H-indole (400.88 g) in 250 mL THF, 2 L of 1N K'BuO, and 381 g of 4-chloro-2-methylsulfanyl-pyrimidine in 350 mL THF were combined with cooling to maintain under 40° C. and allowed to stir at room temperature, for 1 hour. The solvent was then removed in vacuo and the solid was suspended in MeOH, filtered, washed with MeOH and water, and dried to yield 87.56% of 4-(3-methylsulfanyl-propoxy)-1-(2-methylsulfanyl-pyrimidin-4-yl)-1H-indole.

Example 4

1-(2-Methanesulfinyl-pyrimidin-4-yl)-4-(3-methanesulfonyl-propoxy)-1H-indole

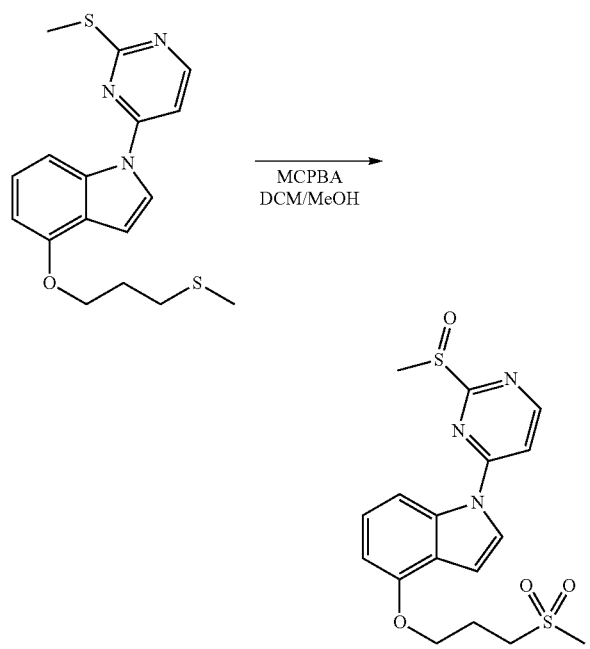

MCPBA (204.3 g, 77%) in DCM (310 mL) and MeOH (155 mL) was added dropwise to 100.0 g 4-(3-methylsulfanyl-propoxy)-1-(2-methylsulfanyl-pyrimidin-4-yl)-1H-indole in DCM (590 mL) and methanol (145 ml) at −5° C. over 1.5 h. Additional MCPBA (12.0 g) was added at 2° C. and the reaction mixture was diluted after 20 minutes with 900 mL MTBE added slowly over 20 min at 12° C. The mixture was allowed to stir for 1.5 h at 20-22° C. MTBE (300 mL) was then added and the mixture filtered after 20 min, the solid rinsed with MTBE (2×200 mL), and the solvent removed in vacuo to yield 1-(2-methanesulfinyl-pyrimidin-4-yl)-4-(3-methanesulfonyl-propoxy)-1H-indole (90.2%).

Example 5

4-{4-[4-(3-Methanesulfonyl-propoxy)-indol-1-yl]-pyrimidin-2-ylamino}-cyclohexanecarboxylic acid methyl ester

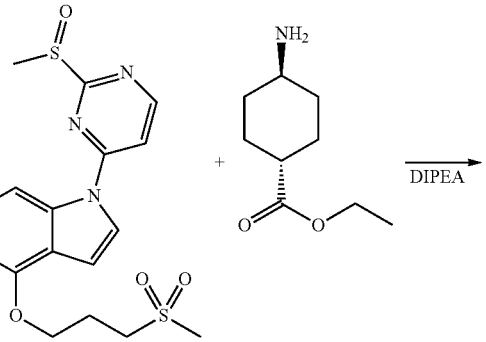

4-Amino-cyclohexanecarboxylic acid ethyl ester (550 g) and 815 mL DIPEA were added to 1-(2-methanesulfinyl-pyrimidin-4-yl)-4-(3-methanesulfonyl-propoxy)-1H-indole (746.7 g) in 2.5 L DMA, and the mixture allowed to heat to 120° C. for 4 h and then allowed to cool to room temperature. Water (3 L) was added dropwise and the resulting precipitate was collected by filtration, washed with H$_2$O and MeOH, and dried in vacuo at 48° C. overnight to yield 4-{4-[4-(3-methanesulfonyl-propoxy)-indol-1-yl]-pyrimidin-2-ylamino}-cyclohexanecarboxylic acid methyl ester (90%).

Example 6

4-(3-Methanesulfonyl-propoxy)-1H-indole

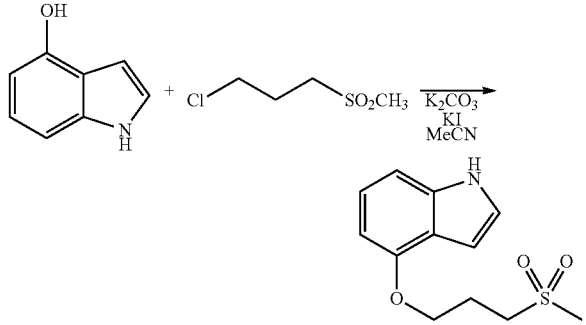

1-Chloro-3-(methanesulfonyl)-propane (160 g) was added to 1H-indol-4-ol (108.77 g) in 1 L MeCN, and 338 g $K_2CO_3$ and 13.36 g KI were added. The reaction mixture was stirred overnight at 80° C., then cooled and filtered through celite. The filtrate was vacuum distilled and solvent replaced with DCM (700 mL). The mixture was filtered, and the solvent removed in vacuo and replaced with MeOH (600 mL). The solvent was partially removed in vacuo at 40° C. and crystallization occurred. After cooling, additional MeOH was added and the slurry was filtered. The collected solid was rinsed with cold MeOH and dried overnight at 35° C. in vacuo under $N_2$ to provide 4-(3-methanesulfonyl-propoxy)-1H-indole (82%).

Example 7

1-(2-Chloro-pyrimidin-4-yl)-4-(3-methanesulfonyl-propoxy)-1H-indole

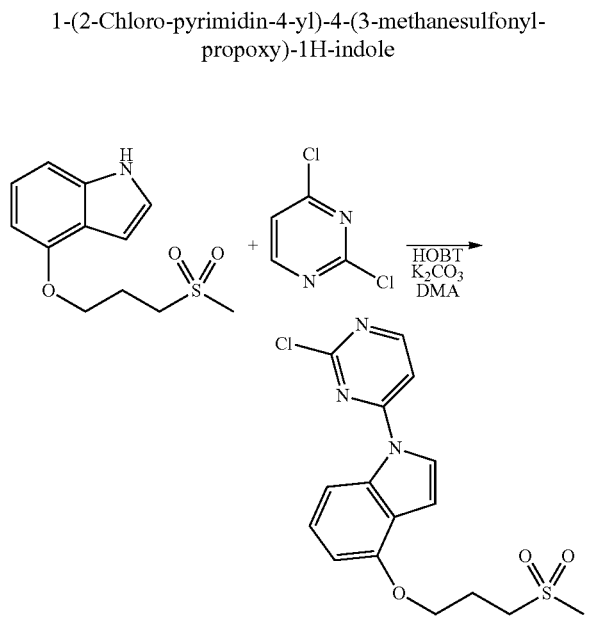

4-(3-Methanesulfonyl-propoxy)-1H-indole (188.1 g), 2,4-dichloropyrimidine (221.25 g), HOBT (20.08 g), $K_2CO_3$ (143.68 g) and DMA (1.6 L) were heated to 85° C. for 20 h. IPA (5 was then added and the mixture was stirred for 20 min, then cooled to 0° C. for 3 h and filtered. The collected solid was rinsed with IPA and water, and the solid was dried in vacuo at 55° C. for 4 days to yield 1-(2-chloro-pyrimidin-4-yl)-4-(3-methanesulfonyl-propoxy)-1H-indole (94%).

Example 8

(2-Propylsulfanyl-pyrimidin-4-yl)-hydrazine

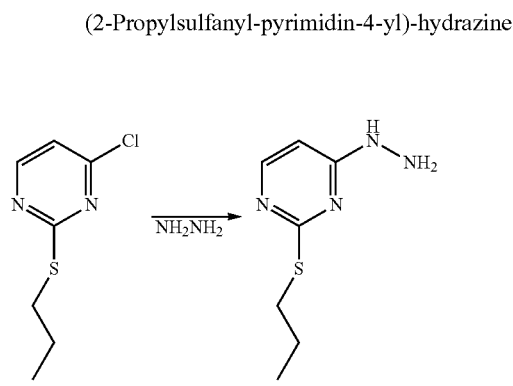

4-Chloro-2-propylsulfanyl-pyrimidine (15.03 g), hydrazine (10.69 g) and potassium carbonate (15.37 g) were added to ethanol (150 mL) and the mixture was heated to 80° C. for three hours. The mixture was cooled, filtered, and the filtrate was concentrated under reduced pressure. The residue was chromatographed ($CH_2Cl_2$/hexanes through silica) to give 7.036 g of (2-propylsulfanyl-pyrimidin-4-yl)-hydrazine.

Example 9

4-Methoxy-1-(2-propylsulfanyl-pyrimidin-4-yl)-1H-indazole

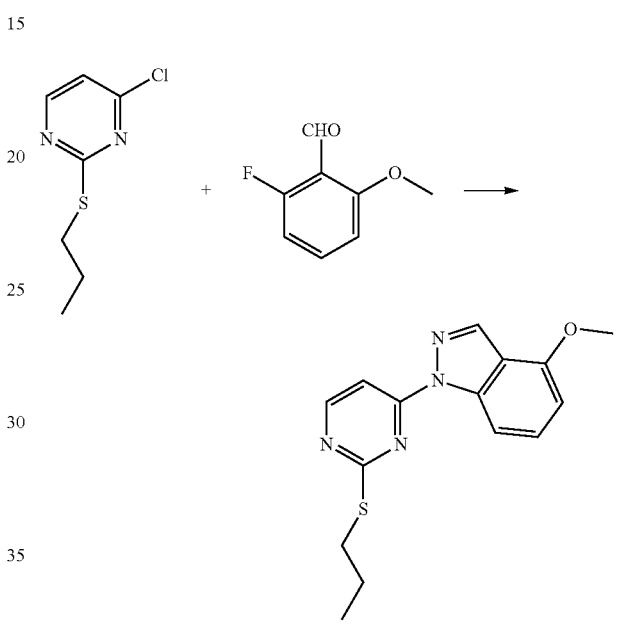

(2-Propylsulfanyl-pyrimidin-4-yl)-hydrazine (7.036 g), 2-fluoro-6-methoxy-4-propylsulfanyl-benzaldehyde 5.524 g) and DB 16.373 g) were added to DMSO (70 mL) and the mixture was stirred at room temperature for one hour, then stirred at 80° C. for one hour. The mixture was cooled, diluted with water, and filtered. The collected solid was washed with water, and dried under reduced pressure to give 4-methoxy-1-(2-propylsulfanyl-pyrimidin-4-yl)-1H-indazole.

Example 10

1-(2-Propylsulfanyl-pyrimidin-4-yl)-1H-indazol-4-ol

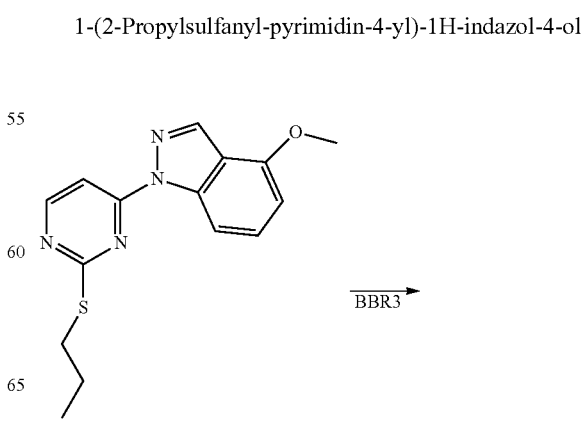

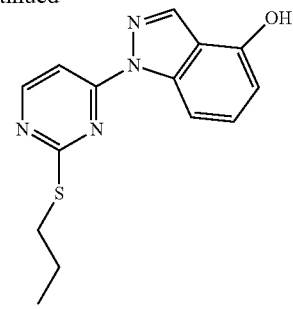

4-Methoxy-1-(2-propylsulfanyl-pyrimidin-4-yl)-1H-indazole was dissolved in methylene chloride (100 mL), and the mixture was cooled to −78° C. and stirred. BBR₃ (152.62 uL) was added, and the mixture was allowed to stir overnight at room temperature. The mixture was partitioned between water and methylene chloride, and the combined organic layers were washed with water, saturated aqueous NaHCO₃ and brine, dried (MgSO₄), filtered and concentrated under reduced pressure to give 1-(2-propylsulfanyl-pyrimidin-4-yl)-1H-indazol-4-ol.

Example 11

4-(2-Methylsulfanyl-ethoxy)-1-(2-propylsulfanyl-pyrimidin-4-yl)-1H-indazole

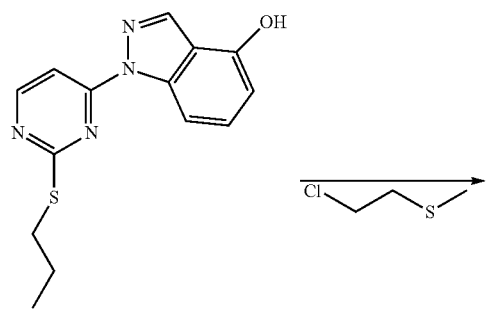

1-(2-Propylsulfanyl-pyrimidin-4-yl)-1H-indazol-4-ol (600 mg), potassium carbonate (1.104 g) and 1-chloro-2-methylsulfanyl-ethane 401.9 mg) were added to NMP (6 mL), and the mixture was heated to 80° C. for three hours. The mixture was cooled, diluted with water and filtered. The collected solid was washed with water and dried under reduced pressure to give 705 mg of 4-(2-Methylsulfanyl-ethoxy)-1-(2-propylsulfanyl-pyrimidin-4-yl)-1H-indazole.

Example 12

Methanesulfonyl-ethoxy)-1-[2-(propane-1-sulfonyl)-pyrimidin-4-yl]-1H-indazole

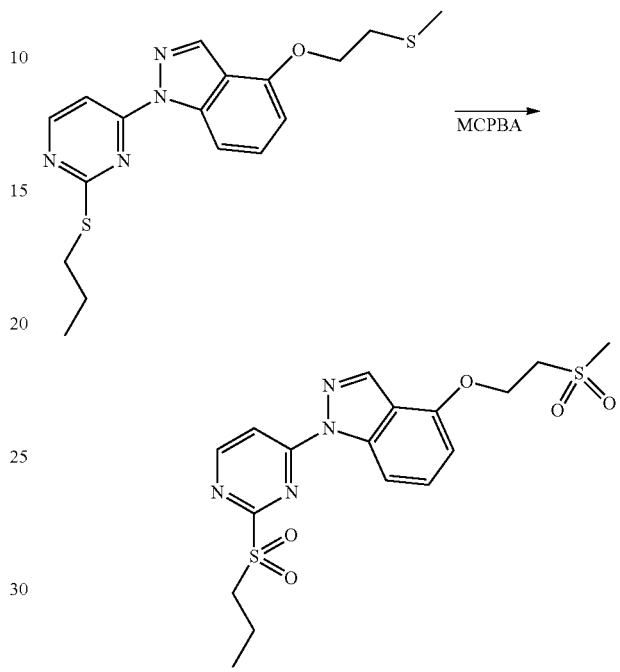

4-(2-Methylsulfanyl-ethoxy)-1-(2-propylsulfanyl-pyrimidin-4-yl)-1H-indazole (705 mg) and meta-perchlorobenzoic acid (2.109 g of 77% solid) were added to methylene chloride (10 mL), and the mixture was stirred overnight at room temperature. The reaction mixture was quenched by addition of 10% aqueous sodium bisulfite and extracted with methylene chloride. The combined organic layers were washed with water, saturated aqueous NaHCO₃ and brine, dried (MgSO₄), filtered and concentrated under reduced pressure to give 4-(2-methanesulfonyl-ethoxy)-1-[2-(propane-1-sulfonyl)-pyrimidin-4-yl]-1H-indazole.

Example 13

4-{4-[4-(2-Methanesulfonyl-ethoxy)-indazol-1-yl]-pyrimidin-2-ylamino}-cyclohexanecarboxylic acid ethyl ester

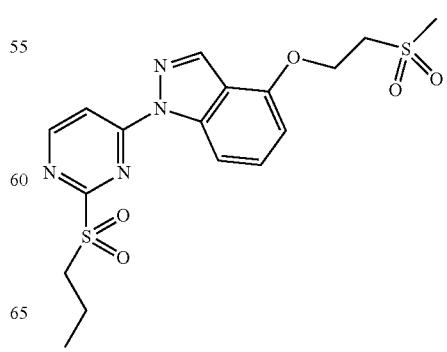

+

-continued

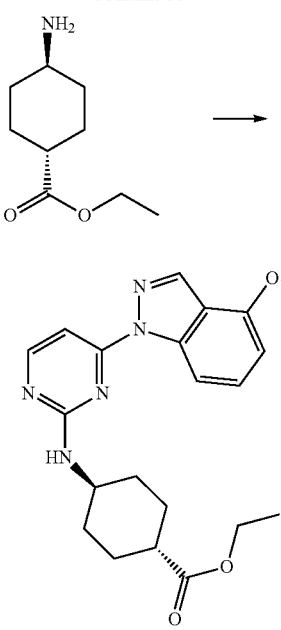

4-{4-[4-(2-Methanesulfonyl-ethoxy)-indazol-1-yl]-pyrimidin-2-ylamino}-cyclohexanecarboxylic acid ethyl ester was prepared by reaction of 4-amino-cyclohexanecarboxylic acid ethyl ester with 4-(2-methanesulfonyl-ethoxy)-1-[2-(propane-1-sulfonyl)-pyrimidin-4-yl]-1H-indazole following generally the procedure of Example 5.

Example 14

4-{4-[4-(3-Methanesulfonyl-propoxy)-indol-1-yl]-pyrimidin-2-ylamino}-cyclohexanecarboxylic acid methyl ester

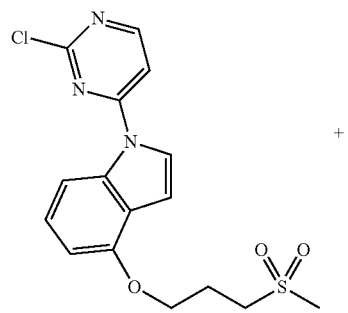

+

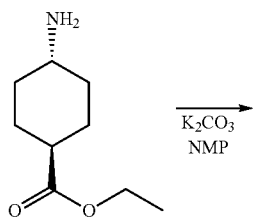

-continued

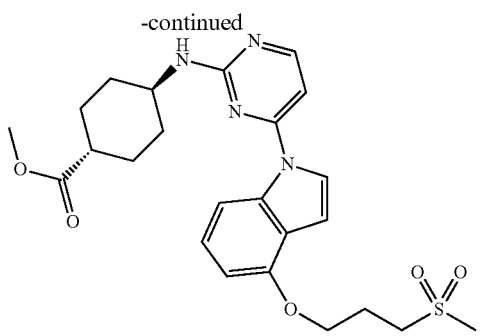

1-(2-Chloro-pyrimidin-4-yl)-4-(3-methanesulfonyl-propoxy)-1H-indole (300 g), 4-amino-cyclohexanecarboxylic acid ethyl ester HCl salt (155 g), and K₂CO₃ (170 g) in NMP (2.35 L) were stirred at 80° C. for 5 h and then stirred overnight at room temperature. The reaction mixture was then stirred on an ice bath, and 2.5 L water was slowly added while stirring, and cooling continued until completion of the exothermic reaction. Upon cooling, the mixture was filtered, and resulting solid was rinsed with H₂O and dried in vacuo overnight to yield 4-{4-[4-(3-methanesulfonyl-propoxy)-indol-1-yl]-pyrimidin-2-ylamino}-cyclohexanecarboxylic acid methyl ester (97%).

Example 15

4-{4-[4-(3-Methanesulfonyl-propoxy)-indol-1-yl]-pyrimidin-2-ylamino}-cyclohexanecarboxylate Sodium Salt

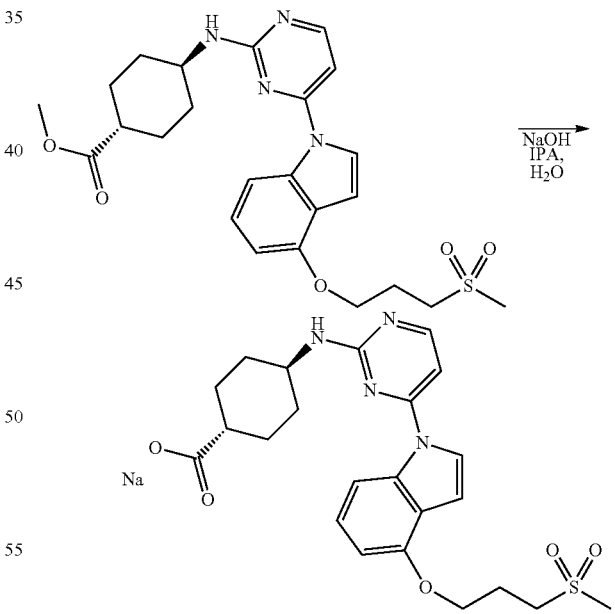

A 50% (w/w) aqueous solution of NaOH in H₂O (198.95 g) was added to 4-{4-[4-(3-Methanesulfonyl-propoxy)-indol-1-yl]-pyrimidin-2-ylamino}-cyclohexanecarboxylic acid methyl ester (830.0 g) in IPA (7.5 L) and the mixture allowed to stir at 82° C. for 1 h and then stirred overnight at room temperature. The mixture was then filtered, and the solid rinsed with IPA, and dried in vacuo at 60° C. for 3 days to yield sodium 4-{4-[4-(3-methanesulfonyl-propoxy)-indol-1-yl]-pyrimidin-2-ylamino}-cyclohexanecarboxylate (96.9%).

Example 16

4-(1,1-Dioxo-tetrahydro-1lambda*6*-thiophen-3-ylmethoxy)-1-(2-propylsulfanyl-pyrimidin-4-yl)-1H-indole

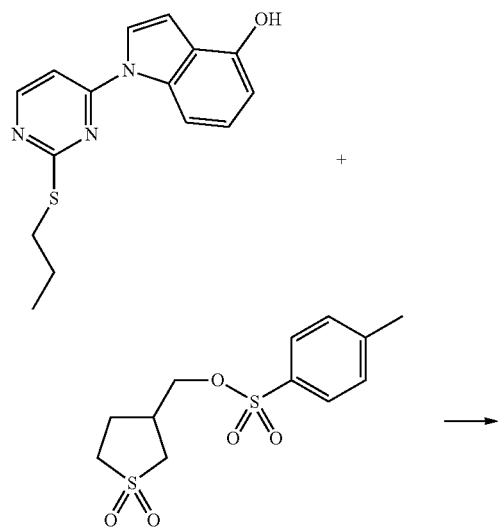

1-(2-Propylsulfanyl-pyrimidin-4-yl)-1H-indol-4-ol (1.56 g) and toluene-4-sulfonic acid 1,1-dioxo-tetrahydro-1lambda*6*-thiophen-3-ylmethyl ester (2.37 g) were added to NMP (20 mL), followed by cesium carbonate (5.08 g). The mixture was stirred at 70° C. for 60 hours, after which solvent was removed by distillation. The residue was diluted with 1N HCl and extracted with EtOAc. The combined organic layers were washed with brine, dried (MgSO$_4$), filtered and concentrated under reduced pressure to give 2.96 g of 4-(1,1-dioxo-tetrahydro-1lambda*6*-thiophen-3-ylmethoxy)-1-(2-propylsulfanyl-pyrimidin-4-yl)-1H-indole.

Example 17

4-(1,1-Dioxo-tetrahydro-1lambda*6*-thiophen-3-ylmethoxy)-1-[2-(propane-1-sulfinyl)-pyrimidin-4-yl]-1H-indole

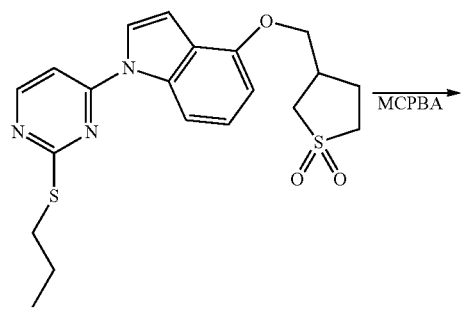

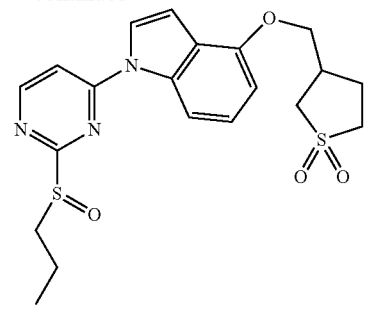

A solution of 4-(1,1-dioxo-tetrahydro-1lambda*6*-thiophen-3-ylmethoxy)-1-(2-propylsulfanyl-pyrimidin-4-yl)-1H-indole (1.16 g) in methylene chloride (40 mL) was cooled to 0° C. and meta-perchloro benzoic acid (3.58 g) was added). The mixture was stirred for 45 minutes and then quenched by addition of saturated aqueous NaHCO$_3$. The mixture was extracted with methylene chloride, and the combined organic layers were dried (MgSO$_4$), filtered and concentrated under reduced pressure to give 1.2 g of 4-(1,1-dioxo-tetrahydro-1lambda*6*-thiophen-3-ylmethoxy)-1-[2-(propane-1-sulfinyl)-pyrimidin-4-yl]-1H-indole.

Example 18

4-{4-[4-(1,1-Dioxo-tetrahydro-1lambda*6*-thiophen-3-ylmethoxy)-indol-1-yl]-pyrimidin-2-ylamino}-cyclohexanecarboxylic acid ethyl ester

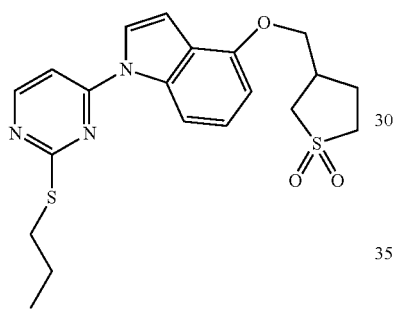

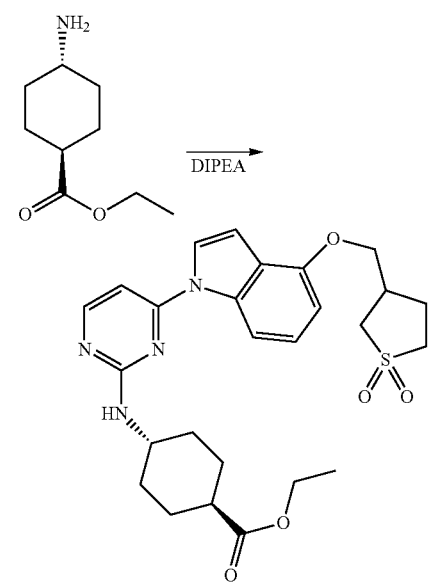

To a solution of 4-(1,1-dioxo-tetrahydro-1lambda*6*-thiophen-3-ylmethoxy)-1-[2-(propane-1-sulfinyl)-pyrimidin-4-yl]-1H-indole 1.2 g) and 4-amino-cyclohexanecarboxylic acid ethyl ester HCl salt (1.12 g) in NMP (5 mL) was added diisopropylethylamine (1.4 mL). The mixture was heated to 80° C. for 18 hours, then cooled and poured into 75 mL water. The mixture was extracted with methylene chloride, and the combined organic layers were dried (MgSO$_4$), filtered and concentrated under reduced pressure. The residue was purified by flash chromatography (60% EtOAc in hexanes) to give 1.069 g of 4-{4-[4-(1,1-dioxo-tetrahydro-1lambda*6*-thiophen-3-ylmethoxy)-indol-1-yl]-pyrimidin-2-ylamino}-cyclohexanecarboxylic acid ethyl ester.

Example 19

4-{4-[4-(3-Methanesulfonyl-propoxy)-indol-1-yl]-pyrimidin-2-ylamino}-cyclohexanecarboxylate Sodium Salt

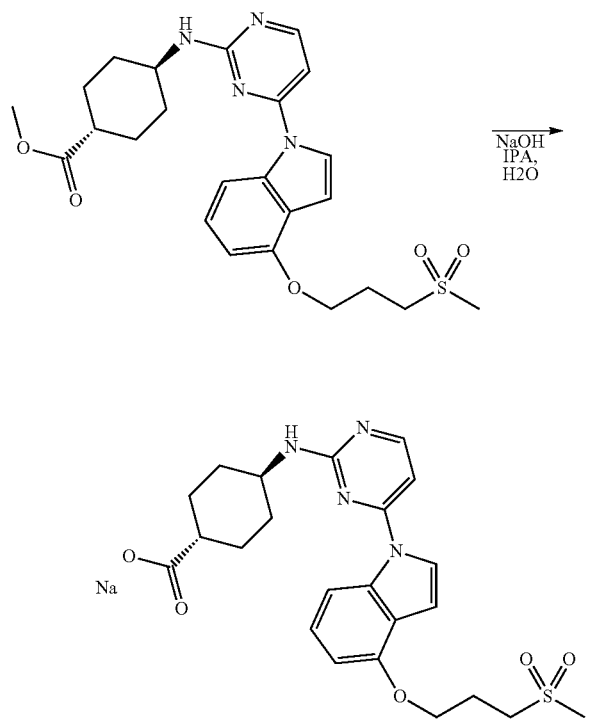

A 50% (w/w) aqueous solution of NaOH in H$_2$O (198.95 g) was added to 4-{4-[4-(3-Methanesulfonyl-propoxy)-indol-1-yl]-pyrimidin-2-ylamino}-cyclohexanecarboxylic acid methyl ester (830.0 g) in IPA (7.5 L) and the mixture allowed to stir at 82° C. for 1h and then stirred overnight at room temperature. The mixture was then filtered, and the solid rinsed with IPA, and dried in vacuo at 60° C. for 3 days to yield sodium 4-{4-[4-(3-methanesulfonyl-propoxy)-indol-1-yl]-pyrimidin-2-ylamino}-cyclohexanecarboxylate (96.9%).

Example 20

(R)-1-(4-{4-[4-(3-Methanesulfonyl-propoxy)-indol-1-yl]-pyrimidin-2-ylamino}-cyclohexanecarbonyl)-piperidine-3-carboxylic acid ethyl ester

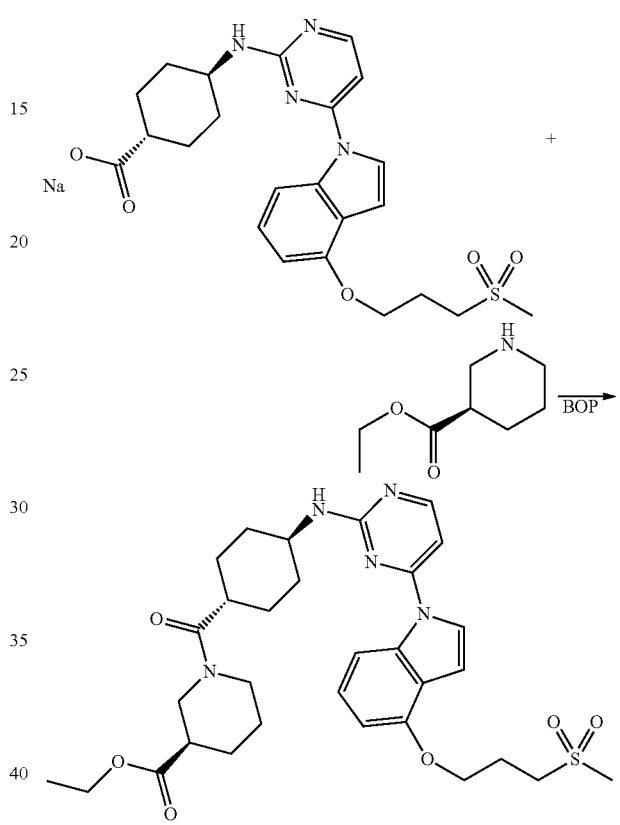

Sodium 4-{4-[4-(3-methanesulfonyl-propoxy)-indol-1-yl]-pyrimidin-2-ylamino}-cyclohexanecarboxylate (0.4 g), (R)-piperidine-3-carboxylic acid ethyl ester (0.165 g), BOP (0.537 g) and DIPEA (0.56 mL) were added to DMF (3 mL), and the mixture was stirred at room temperature overnight. The mixture was diluted with water and the resulting precipitate was collected by filtration, washed with water, dried under reduced pressure, and purified by flash chromatography (DCM/MeOH) to give 39.6 mg of (R)-1-(4-{4-[4-(3-methanesulfonyl-propoxy)-indol-1-yl]-pyrimidin-2-ylamino}-cyclohexanecarbonyl)-piperidine-3-carboxylic acid ethyl ester, MP=175.0-177.0° C.

Additional compounds prepared using the above procedures are shown in Table 1.
Biological Assays Example 21

JNK Assay in vitro

JNK activity was measured by phosphorylation of GST-ATF2 (19-96) with [γ-$^{33}$P] ATP. The enzyme reaction was conducted at Km concentrations of ATP and the substrate at final volume of 40 μl in buffer containing 25 mM HEPES, pH 7.5, 2 mM dithiothreitol, 150 mM NaCl, 20 mM MgCl$_2$, 0.001% Tween® 20, 0.1% BSA and 10% DMSO. Human JNK2α2 assay contains 1 nM enzyme, 1 μM ATF2, 8 μM ATP with 1 uCi [γ-$^{33}$P] ATP. Human JNK1α1 assay contains 2 nM enzyme, 1 μM ATF2, 6 μM ATP with 1 μCi [γ-$^{33}$P] ATP. Human JNK3 (Upstate Biotech #14-501M) assay contains 2 nM enzyme, 1 μM ATF2, 4 μM ATP with 1 μCi [γ-$^{33}$P] ATP. The enzyme assay was carried out in the presence or absence of several compound concentrations. JNK and compound were pre-incubated for 10 min., followed by initiation of the enzymatic reaction by adding ATP and the substrate. The reaction mixture was incubated at 30° C. for 30 min. At the end of incubation, the reaction was terminated by transferring 25 μl of the reaction mixture to 150 μl of 10% glutathione Sepharose® slurry (Amersham #27-4574-01) containing 135 mM EDTA. The reaction product was captured on the affinity resin, and washed on a filtration plate (Millipore, MAB-VNOB50) with phosphate buffered saline for six times to remove free radionucleotide. The incorporation of $^{33}$P into ATF2 was quantified on a microplate scintillation counter (Packard Topcount). Compound inhibition potency on JNK was measured by $IC_{50}$ value generated from ten concentration inhibition curves fitted into the 3-parameter model: % inhibition=Maximum/$(1+(IC_{50}/[Inhibitor])^{slope})$. Data were analyzed on Microsoft Excel for parameter estimation. Representative results are shown in Table 1 below:

Example 22

Rat in vivo TNFα-induced IL-6 Production Assay

Female Wistar-Han rats procured from Charles River Laboratories are allowed to acclimate for one week prior to use and achieve an approximate body weight of 101-130 g. Rats are administered test compound (N=8 per compound) via oral gavage 30 min prior to an intraperitoneal challenge of 0.5 μg recombinant rat TNF-α (Biosource). Blood is collected via cardiocentesis 90 min after TNF-α challenge. Plasma is prepared using lithium heparin separation tubes (BD microtainer) and frozen at −80° C. until analyzed. IL-6 levels are determined using a rat specific IL-6 ELISA kit (Biosource). The percent inhibition and $ED_{50}$ values (calculated as the dose of compound at which TNF-α production is 50% of the control value) are determined.

Example 23

Rat in vivo TNFα-induced IL-6 Production Assay

Female Wistar-Han rats procured from Charles River Laboratories are allowed to acclimate for one week prior to use and achieve an approximate body weight of 114-132 g. Rats are administered compound 18 (N=8 per dose) subcutaneously 30 min prior to an intra-peritoneal challenge of 0.5 μg recombinant rat TNF-α (Biosource). Blood is collected via cardio-centesis 90 min after TNF-α challenge. Plasma is prepared using lithium heparin separation tubes (BD microtainer) and frozen at −80° C. until analyzed. IL-6 levels are determined using a rat specific IL-6 ELISA kit (Biosource). The percent inhibition and $ED_{50}$ values (calculated as the dose of compound at which TNF-α production is 50% of the control value) are determined.

Example 24

Rodent Collagen-induced Arthritis

Female Lewis rats procured from Harlan Laboratories at 7-8 weeks of age are allowed to acclimate for one week prior to use and achieve an approximate body weight of 120-140 g. On day 0 of study, rats are primed intradermally (i.d.) on several sites on the back with an emulsion of 100 μg Bovine Type II Collagen (Chondrex) in Incomplete Freund's adjuvant (IFA; total of 0.1 ml in 2-3 sites). Arthritis induction is generally observed 12-14 days from priming; however a booster injection of 100 μg collagen/IFA is given around days 7-10 (i.d. up to 0.1 ml total) at the base of the tail or an alternate site on back to synchronize disease induction. Compound dosing can be prophylactic (starting at time of boost or 1-2 days prior) or therapeutic (beginning after boost and coinciding with initial disease scores of 1-2—see clinical scoring below). Animals are evaluated for the development and progression of disease over the next 21 days.

Rats are evaluated using a scoring system (described below), paw volume measurements using a plethysmometer for each paw, or measuring paw or joint thickness with a caliper. Baseline measurements are performed on day 0, and starting again at the first signs of swelling for up to three times per week until the end of the experiment. Scoring is evaluated as follows for each paw:
1=swelling and/or redness of paw or one digit.
2=swelling in two or more joints.
3=gross swelling of the paw with more than two joints involved.
4=severe arthritis of the entire paw and digits.

The arthritic index for each rat is evaluated by adding the four scores of the individual paws, giving a maximum score of 16. In order to serially measure disease onset and progression, the paw volume of the hind paws is also determined through the use of a plethysmometer.

At the end of the study, the hind paws (and other tissues) are harvested for weight determination, histology, cellular and/or molecular analysis. Additionally, blood is collected via cardiocentesis, plasma is prepared using lithium heparin separation tubes (BD microtainer) and frozen at −70° C. until analyzed. Inflammatory cytokine levels (e.g., TNF-α, IL-1 and IL-6) from the plasma or from homogenized joint tissue are determined using rat-specific ELISA kits (R&D). The level of disease protection or inhibition is determined as a composite of changes in clinical scores, paw volumes and histopathology compared to control animals.

Example 25

Rat Pharmacokinetic Study

Female Wistar/Han (CRL: WI) Rats (Charles River, Hollister, Calif.) weighing between 180 and 220 g are used. Animals are allowed free access to a standard laboratory chow and tap water and are housed in a constant temperature-humidity environment. Three rats per dose regime are administered either single 10 mg/kg IV bolus doses (50% cyclodextran/water) or single 10 mg/kg oral suspension doses prepared in aqueous vehicle containing 0.9% NaCl, 0.5% sodium carboxymethyl cellulose, 0.4% polysorbate 80 and 0.9% benzyl alcohol. Blood is collected from each rat anesthetized with $CO_2:O_2$ (60:40) via the orbital sinus or cardiac puncture at 1, 3, 6, 8, and 24 h after dosing. Plasma levels of test compounds are assayed by a LC/MS method. In this method, an aliquot of plasma is treated by mixing with acetonitrile to precipitate protein, centrifuged to clarify the supernatant, then further diluted with formate buffer (50 mM), and injected onto an HPLC. Test compounds are separated from endogenous interfering substances and subsequently eluted from the HPLC column for mass spectrometric quantification.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of formula I

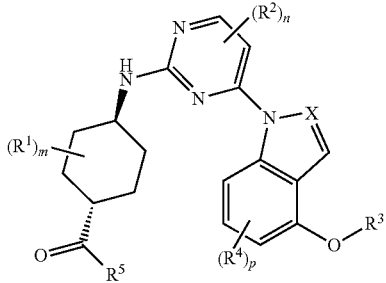

or a pharmaceutically acceptable salt thereof,
wherein:
  m is from 0 to 2;
  n is from 0 to 2;
  p is from 0 to 3;
  X is CH or N;
  each $R^1$ is independently: hydrogen; or $C_{1-6}$alkyl;
  each $R^2$ is independently: $C_{1-6}$alkyl; $C_{1-6}$alkoxy halo-$C_{1-6}$alkyl; or halo-$C_{1-6}$alkoxy;
  $R^3$ is: $C_{1-6}$alkylsulfonyl-$C_{1-6}$alkyl; thiophenyl-1,1-oxide-$C_{1-6}$alkyl; or tetrahydrothiopyran-1,1-oxide-$C_{1-6}$alkyl;
  each $R^4$ is independently: $C_{1-6}$alkyl; $C_{1-6}$alkoxy halo-$C_{1-6}$alkyl; or halo-$C_{1-6}$alkoxy;
  $R^5$ is a group of formula (a) or (b):

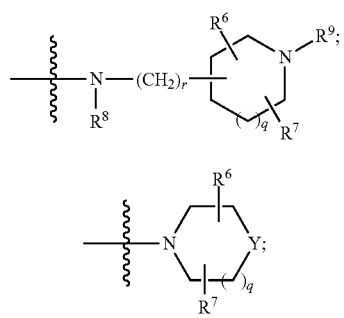

wherein:
  q is 0 or 1;
  r is 0 or 1;
  Y is: $NR^9$; or $CR^{10}R^{11}$;
  $R^6$ and $R^7$ each independently is: hydrogen; or $C_{1-6}$alkyl; or $R^6$ and $R^7$ together form a $C_{1-2}$alkylene;
  $R^8$ is: hydrogen; or $C_{1-6}$alkyl;
  $R^9$ is: hydrogen; or $C_{1-6}$alkyl;
  $R^{10}$ is: hydrogen; or $C_{1-6}$alkyl; and
  $R^{11}$ is: $C_{1-6}$alkyl; hydroxy-$C_{1-6}$alkyl; carboxy; carboxy-$C_{1-6}$alkyl; carboxy-$C_{1-6}$alkyl ester; or carboxy-$C_{1-6}$ alkyl ester.

2. The compound of claim 1, wherein m is 0.
3. The compound of claim 1, wherein n is 0.
4. The compound of claim 1, wherein p is 0.
5. The compound of claim 1, wherein q is 1.
6. The compound of claim 1, wherein q is 0.
7. The compound of claim 1, wherein X is CH.
8. The compound of claim 1, wherein X is N.
9. The compound of claim 1, wherein Y is $NR^9$.
10. The compound of claim 1, wherein Y is $CR^{10}R^{11}$.
11. The compound of claim 1, wherein $R^3$ is $C_{1-6}$alkylsulfonyl-$C_{1-6}$alkyl.
12. The compound of claim 1, wherein $R^3$ is tetrahydrothiophenyl-1,1-oxide-$C_{1-6}$alkyl.
13. The compound of claim 1, wherein $R^5$ is a group of formula (a).
14. The compound of claim 1, wherein $R^5$ is a group of formula (b).
15. The compound of claim 1, wherein said compound is selected from the group consisting of:
  [1-(4-{4-[4-(3-Methanesulfonyl-propoxy)-indol-1-yl]-pyrimidin-2-ylamino}-cyclohexanecarbonyl)-piperidin-4-yl]-acetic acid ethyl ester;
  (R)-1-(4-{4-[4-(3-Methanesulfonyl-propoxy)-indol-1-yl]-pyrimidin-2-ylamino}-cyclohexanecarbonyl)-piperidine-3-carboxylic acid ethyl ester;
  (4-{4-[4-(1,1-Dioxo-tetrahydro-1$\lambda^6$-thiophen-3-yl-methoxy)-indol-1-yl]-pyrimidin-2-ylamino}-cyclohexyl)-((R)-4-ethyl-3-methyl-piperazin-1-yl)-methanone
  (S)-1-(4-{4-[4-(3-Methanesulfonyl-propoxy)-indol-1-yl]-pyrimidin-2-ylamino}-cyclohexanecarbonyl)-piperidine-3-carboxylic acid;
  1-(4-{4-[4-(3-Methanesulfonyl-propoxy)-indol-1-yl]-pyrimidin-2-ylamino}-cyclohexanecarbonyl)-piperidine-4-carboxylic acid amide;
  [4-(1-Hydroxy-1-methyl-ethyl)-piperidin-1-yl]-(4-{4-[4-(3-methanesulfonyl-propoxy)-indol-1-yl]-pyrimidin-2-ylamino}-cyclohexyl)-methanone;
  1-(4-{4-[4-(1,1-Dioxo-tetrahydro-1$\lambda^6$-thiophen-3-yl-methoxy)-indol-1-yl]-pyrimidin-2-ylamino}-cyclohexanecarbonyl)-piperidine-4-carboxylic acid ethyl ester;
  1-(4-{4-[4-(1,1-Dioxo-tetrahydro-1$\lambda^6$-thiophen-3-yl-methoxy)-indol-1-yl]-pyrimidin-2-ylamino}-cyclohexanecarbonyl)-piperidine-4-carboxylic acid;
  (4-{4-[4-(1,1-Dioxo-tetrahydro-1$\lambda^6$-thiophen-3-yl-methoxy)-indol-1-yl]-pyrimidin-2-ylamino}-cyclohexyl)-((S)-4-ethyl-3-methyl-piperazin-1-yl)-methanone;
  1-(4-{4-[4-(3-Methanesulfonyl-propoxy)-indol-1-yl]-pyrimidin-2-ylamino}-cyclohexanecarbonyl)-4-methyl-piperidine-4-carboxylic acid ethyl ester;
  4-{4-[4-(3-Methanesulfonyl-propoxy)-indol-1-yl]-pyrimidin-2-ylamino}-cyclohexanecarboxylic acid ((R)-1-propyl-pyrrolidin-3-yl)-amide;
  4-{4-[4-(3-Methanesulfonyl-propoxy)-indol-1-yl]-pyrimidin-2-ylamino}-cyclohexanecarboxylic acid ((R)-1-ethyl-pyrrolidin-3-yl)-amide;
  4-{4-[4-(3-Methanesulfonyl-propoxy)-indol-1-yl]-pyrimidin-2-ylamino}-cyclohexanecarboxylic acid ((S)-1-ethyl-pyrrolidin-3-yl)-amide;
  4-{4-[4-(3-Methanesulfonyl-propoxy)-indol-1-yl]-pyrimidin-2-ylamino}-cyclohexanecarboxylic acid ((R)-1-propyl-piperidin-3-yl)-amide;
  4-{4-[4-(3-Methanesulfonyl-propoxy)-indol-1-yl]-pyrimidin-2-ylamino}-cyclohexanecarboxylic acid ((R)-1-ethyl-piperidin-3-yl)-amide;
  4-{4-[4-(3-Methanesulfonyl-propoxy)-indol-1-yl]-pyrimidin-2-ylamino}-cyclohexanecarboxylic acid ((S)-1-propyl-piperidin-3-yl)-amide;
  4-{4-[4-(3-Methanesulfonyl-propoxy)-indol-1-yl]-pyrimidin-2-ylamino}-cyclohexanecarboxylic acid ((S)-1-ethyl-piperidin-3-yl)-amide;

1-(4-{4-[4-(3-Methanesulfonyl-propoxy)-indol-1-yl]-pyrimidin-2-ylamino}-cyclohexanecarbonyl)-4-methyl-piperidine-4-carboxylic acid;

4-{4-[4-(3-Methanesulfonyl-propoxy)-indol-1-yl]-pyrimidin-2-ylamino}-cyclohexanecarboxylic acid methyl-(1-methyl-piperidin-2-ylmethyl)-amide;

4-{4-[4-(3-Methanesulfonyl-propoxy)-indol-1-yl]-pyrimidin-2-ylamino}-cyclohexanecarboxylic acid (1-ethyl-pyrrolidin-2-ylmethyl)-amide;

(1R,4S)-2,5-Diaza-bicyclo[2.2.1]hept-2-yl-(4-{4-[4-(3-methanesulfonyl-propoxy)-indol-1-yl]-pyrimidin-2-ylamino}-cyclohexyl)-methanone;

(4-{4-[4-(3-Methanesulfonyl-propoxy)-indol-1-yl]-pyrimidin-2-ylamino}-cyclohexyl)-(8-methyl-3,8-diaza-bicyclo[3.2.1]oct-3-yl)-methanone;

(4-{4-[4-(3-Methanesulfonyl-propoxy)-indazol-1-yl]-pyrimidin-2-ylamino}-cyclohexyl)-((S)-3-methyl-piperazin-1-yl)-methanone;

(4-{4-[4-(3-Methanesulfonyl-propoxy)-indazol-1-yl]-pyrimidin-2-ylamino}-cyclohexyl)-((R)-3-methyl-piperazin-1-yl)-methanone;

(4-{4-[4-(1,1-Dioxo-tetrahydro-1$\lambda^6$-thiophen-3-ylmethoxy)-indazol-1-yl]-pyrimidin-2-ylamino}-cyclohexyl)-((S)-3-methyl-piperazin-1-yl)-methanone;

(3-Ethoxy-8-aza-bicyclo[3.2.1]oct-8-yl)-(4-{4-[4-(3-methanesulfonyl-propoxy)-indol-1-yl]-pyrimidin-2-ylamino}-cyclohexyl)-methanone;

(4-{4-[4-(1,1-Dioxo-tetrahydro-1$\lambda^6$-thiophen-3-ylmethoxy)-indazol-1-yl]-pyrimidin-2-ylamino}-cyclohexyl)-((S)-3-methyl-piperazin-1-yl)-methanone;

(3,3-Dimethyl-piperazin-1-yl)-(4-{4-[4-(1,1-dioxo-tetrahydro-1$\lambda^6$-thiophen-3-ylmethoxy)-indol-1-yl]-pyrimidin-2-ylamino}-cyclohexyl)-methanone;

4-{4-[4-(1,1-Dioxo-tetrahydro-1$\lambda^6$-thiophen-3-ylmethoxy)-indol-1-yl]-pyrimidin-2-ylamino}-cyclohexanecarboxylic acid (1-ethyl-piperidin-3-yl)-amide;

4-{4-[4-(3-Methanesulfonyl-propoxy)-indol-1-yl]-pyrimidin-2-ylamino}-cyclohexanecarboxylic acid ((S)-1-ethyl-pyrrolidin-2-ylmethyl)-amide; and 4-{4-[4-(3-Methanesulfonyl-propoxy)-indol-1-yl]-pyrimidin-2-ylamino}-cyclohexanecarboxylic acid ((R)-1-ethyl-pyrrolidin-2-ylmethyl)-amide.

16. A composition comprising the compound of claim 1, admixed with at least one pharmaceutically acceptable carrier, excipient or diluent.

* * * * *